US010119135B2

(12) United States Patent
Mall et al.

(10) Patent No.: US 10,119,135 B2
(45) Date of Patent: Nov. 6, 2018

(54) THERAPEUTIC MICRO RNA TARGETS IN CHRONIC PULMONARY DISEASES

(71) Applicant: RUPRECHT-KARLS-UNIVERSITAET HEIDELBERG, Heidelberg (DE)

(72) Inventors: Marcus Mall, Heidelberg (DE); Raman Agrawal, Heidelberg (DE); Martina Muckenthaler, Heidelberg (DE)

(73) Assignee: RUPRECHT-KARLS-UNIVERSITÄT HEIDELBERG, Heidelberg (DE)

( * ) Notice: Subject to any disclaimer, the term of this patent is extended or adjusted under 35 U.S.C. 154(b) by 70 days.

(21) Appl. No.: 14/402,586

(22) PCT Filed: May 15, 2013

(86) PCT No.: PCT/EP2013/060027
§ 371 (c)(1),
(2) Date: Nov. 20, 2014

(87) PCT Pub. No.: WO2013/174692
PCT Pub. Date: Nov. 28, 2013

(65) Prior Publication Data
US 2015/0140067 A1    May 21, 2015

Related U.S. Application Data

(60) Provisional application No. 61/650,005, filed on May 22, 2012.

(51) Int. Cl.
| | | |
|---|---|---|
| C12N 15/11 | (2006.01) | |
| C12N 15/113 | (2010.01) | |
| A61K 31/713 | (2006.01) | |
| A61K 45/06 | (2006.01) | |
| C12Q 1/6883 | (2018.01) | |
| A61K 47/54 | (2017.01) | |

(52) U.S. Cl.
CPC .......... *C12N 15/113* (2013.01); *A61K 31/713* (2013.01); *A61K 45/06* (2013.01); *A61K 47/543* (2017.08); *C12Q 1/6883* (2013.01); *C12N 2310/113* (2013.01); *C12N 2310/141* (2013.01); *C12N 2310/315* (2013.01); *C12N 2310/321* (2013.01); *C12N 2310/3515* (2013.01); *C12Q 2600/178* (2013.01)

(58) Field of Classification Search
None
See application file for complete search history.

(56) References Cited

U.S. PATENT DOCUMENTS

| | | | | |
|---|---|---|---|---|
| 2005/0265927 A1* | 12/2005 | Lee | ...................... | A61K 9/0043 424/46 |
| 2006/0058255 A1* | 3/2006 | Chen | ..................... | C12N 15/111 514/44 A |
| 2011/0224283 A1* | 9/2011 | Iversen | .............. | C12N 15/1138 514/44 A |
| 2011/0251098 A1* | 10/2011 | Showe | ............... | G01N 33/5091 506/9 |

FOREIGN PATENT DOCUMENTS

| | | |
|---|---|---|
| EP | 2 298 359 A1 | 3/2011 |
| WO | WO 2007/087539 A2 | 8/2007 |
| WO | WO 2009/137807 A2 | 11/2009 |
| WO | WO 2010/054233 A1 | 5/2010 |
| WO | WO 2011/015720 A1 | 2/2011 |
| WO | WO 2011/080318 A1 | 7/2011 |
| WO | WO 2013/078283 A1 | 5/2013 |

OTHER PUBLICATIONS

Mattes et al., Antagonism of microRNA-126 suppresses the effector function of TH2 cells and the development of allergic airways disease, 2009, PNAS, vol. 106, pp. 18704-18709.*
Agostini et al., Neuronal differentiation by TAp73 is mediated by microRNA-34a regulation of synaptic protein targets, 2011, PNAS, vol. 52, pp. 21093-21098.*
Nguyen et al., Downregulation of microRNA-29c is associated with hypermethylation of tumor-related genes and disease outcome in cutaneous melanoma, 2011, Epigenetics, vol. 6, pp. 388-394.*
Bhattacharyya et al., Elevated miR-155 promotes inflammation in cystic fibrosis by driving hyperexpression of interleukin-8, 2011, The Journal of Biological Chemistry, vol. 286, pp. 11604-11615.*
Bellon et al., Aerosol administration of a recombinant adenovirus expression CTFR to cystic fibrosis patients: A Phase I clinical trial, 1997, Human Gene Therapy, vol. 8, pp. 15-25.*
Celli et al., Standards for the diagnosis and treatment of patients with COPD: a summary of the ATS/ERS position paper, 2004, European Respiratory Journal, vol. 23, pp. 932-946.*

(Continued)

Primary Examiner — Dana H Shin
(74) Attorney, Agent, or Firm — Saliwanchik, Lloyd & Eisenschenk

(57) ABSTRACT

The present invention relates to the identification of microRNAs of the miR-148 family that are involved in the pathogenesis of chronic pulmonary diseases. The present invention relates to micro RNA of the miR-148 family selected from miR-148a, miR-148b and miR-152 for use in the diagnosis, prognosis, prevention and/or therapy of a chronic pulmonary disease. The present invention further relates to miR-148 inhibitors, pharmaceutical compositions comprising such inhibitors, their use in preventing and/or treating chronic pulmonary diseases, and methods for preventing and/or treating chronic pulmonary diseases. The present invention further relates to transgenic, non-human mammals and methods for identifying modulators of miR-148 and methods for diagnosis and/or prognosis of chronic pulmonary diseases.

15 Claims, 11 Drawing Sheets
(1 of 11 Drawing Sheet(s) Filed in Color)
Specification includes a Sequence Listing.

(56) References Cited

OTHER PUBLICATIONS

Christenson et al., miR-638 regulates gene expression networks associated with emphysematous lung destruction, 2013, Genome Medicine, vol. 5:114, pp. 1-13.*

Mall, M. et al., "Increased airway epithelial Na+ absorption produces cystic fibrosis-like lung disease in mice." Nature Medicine, May 2014, 10(5): 487-493.

Ezzie, Michael E. et al., "Gene expression networks in COPD: microRNA and mRNA regulation," Thorax2012, 7:122-131.

Guo, Shui-Long et al., "miR-148a Promoted Cell Proliferation by Targeting p27 in Gastric Cancer Cells," International Journal of Biological Sciences, 2011, 7(5):567-574.

Izzotti, Alberto et al., "Relationships of microRNA expression in mouse lung with age and exposure to cigarette smoke and light," The FASEB Journal, 2009, 23:3243-3250.

Kool, Mirjam et al., "Dendritic cells in asthma and COPD: opportunities for drug development," Current Opinion in Immunology, 2007, 19:701-710.

Liu, Xingguang et al., "MicroRNA-148/152 Impair Innate Response and Antigen Presentation of TLR-Triggered Dendritic Cells by Targeting CaMKIIα," The Journal of Immunology, 2010, 185:7244-7251.

Nicodemus-Johnson, Jessie et al., "Maternal asthma and mircoRNA regulation of soluble HLA-G in the airway," J Allergy Clin Immunol., 2013, 131(6):1496-1503.

Nymark, Penny et al., "Integrative Analysis of microRNA, mRNA and aCGH Data Reveals Asbestos—and Histology-Related Changes in Lung Cancer," Genes, Chromosomes & Cancer, 2011, 50(8):1-13.

Provinciali, Mauro et al., "Inflammation, chronic obstructive pulmonary disease and aging," Current Opinion in Pulmonary Medicine, 2011, 17 (suppl 1):S3-S10.

Tan, Z. et al., "A Polymorphism in the HLA-G 3'-UTR Influences Targeting of mir-148 and is Associated with Asthma," J. Allergy Clin Immunol., 2006, 117(2):Abstracts S141.

Tan, Zheng et al., "Allele-Specific Targeting of microRNAs to HLA-G and Risk of Asthma," The American Journal of Human Genetics, 2007, 81:829-834.

Tomankova, Tereza et al., "Involvement of microRNAs in physiological and pathological processes in the lung," Respiratory Research, 2010, 11:159.

Van Pottelberge, Geert R. et al., "MircoRNA Expression in Induced Sputum of Smokers and Patients with Chronic Obstructive Pulmonary Disease," Am. J. Respir. Crit. Care Med., 2011, 183:898-906.

* cited by examiner

Figure 3A

Prediction algorithms:

- TargetScan
- Pictar
- DIANA-microT

Potential targets of miR-148b associated with lung phenotype

| symbol | name | function |
|--------|------|----------|
| PTEN | phosphatase and tensin homolog | tumor suppressor, normal lung morphogenesis |
| S1PR1 | sphingosine-1-phosphate receptor 1 | T-cell retention, inflammation |
| ERRFI1 | ERBB receptor feedback inhibitor 1 | tumor suppressor, normal lung morphogenesis |
| FBN1 | fibrillin 1 | supporting connective tissue |
| MEOX2 | mesenchyme homeobox 2 | tumor suppressor |
| CAND1 | cullin-associated and neddylation-dissociated 1 | cell cycle, cytokine signaling |

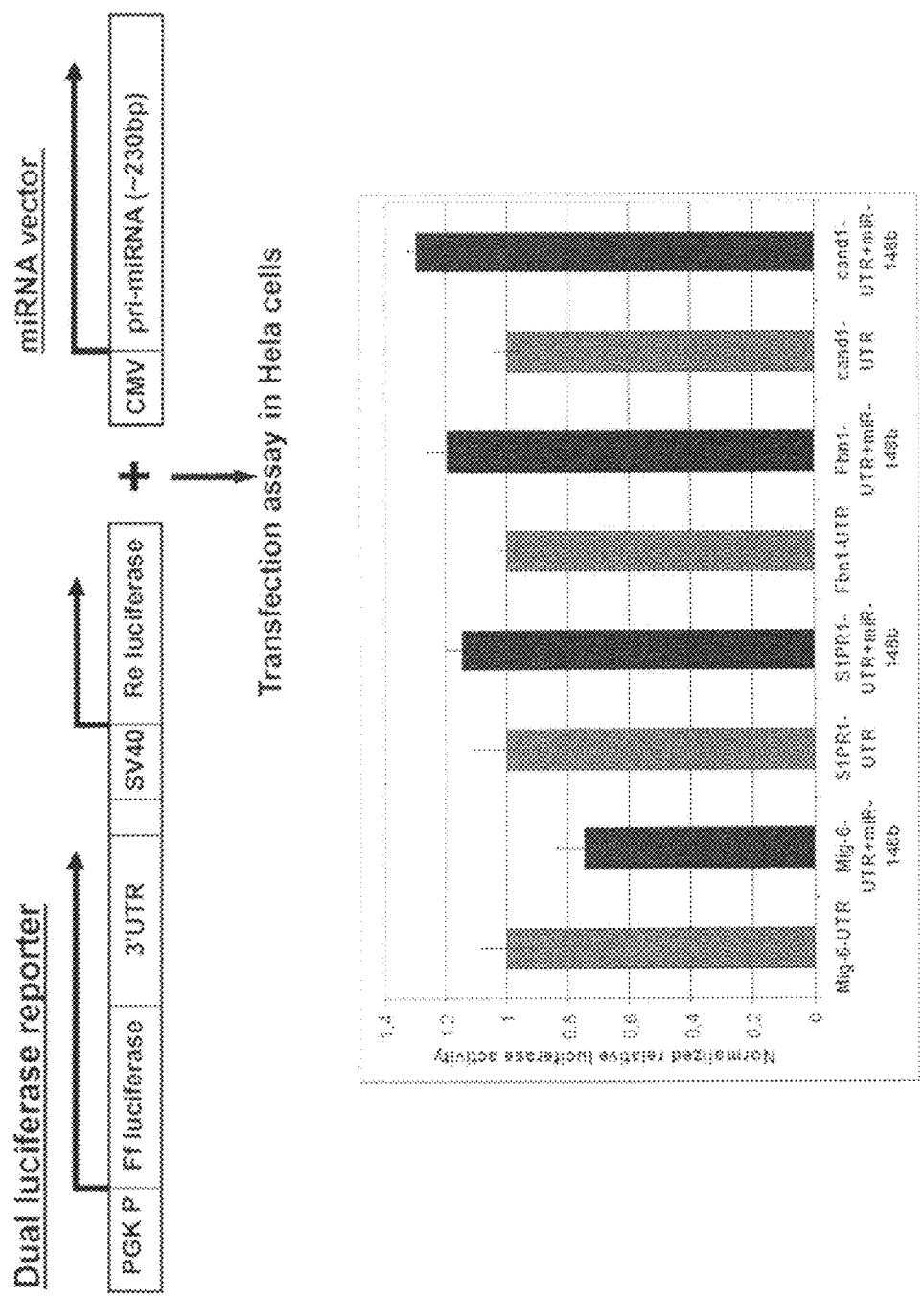

SEQUENCE LISTING

```
<160> NUMBER OF SEQ ID NOS: 17

<210> SEQ ID NO 1
<211> LENGTH: 22
<212> TYPE: RNA
<213> ORGANISM: Homo sapiens

<400> SEQUENCE: 1
ucagugcauc acagaacuuu gu                                              22

<210> SEQ ID NO 2
<211> LENGTH: 22
<212> TYPE: RNA
<213> ORGANISM: Homo sapiens

<400> SEQUENCE: 2
ucagugcacu acagaacuuu gu                                              22

<210> SEQ ID NO 3
<211> LENGTH: 21
<212> TYPE: RNA
<213> ORGANISM: Homo sapiens
```

<400> SEQUENCE: 3
ucagugcaug acagaacuug g                                             21

<210> SEQ ID NO 4
<211> LENGTH: 99
<212> TYPE: RNA
<213> ORGANISM: Homo sapiens

<400> SEQUENCE: 4
caagcacgau uagcauuuga ggugaaguuc uguuauacac ucaggcugug gcucucugaa    60
agucagugca ucacagaacu uugucucgaa agcuuucua                          99

<210> SEQ ID NO 5
<211> LENGTH: 97
<212> TYPE: RNA
<213> ORGANISM: Mus musculus

<400> SEQUENCE: 5
caggcacccu uagcauuuga ggugaaguuc uguuauacac ucaggcugug gcucugaaag    60
ucagugcauc acagaacuuu gucucgaaag cuuucua                            97

<210> SEQ ID NO 6
<211> LENGTH: 68
<212> TYPE: RNA
<213> ORGANISM: Homo sapiens

<400> SEQUENCE: 6
gaggcaaagu ucugagacac uccgacucug aguaugauag aagucagugc acuacagaac    60
uuugucuc                                                            68

<210> SEQ ID NO 7
<211> LENGTH: 99
<212> TYPE: RNA
<213> ORGANISM: Mus musculus

<400> SEQUENCE: 7
agccaguuug gucuuuugag acaaaguucu gagacacucc gacucugagu augauagaag    60
ucagugcacu acagaacuuu gucucuagag cugugguc                           99

<210> SEQ ID NO 8
<211> LENGTH: 87
<212> TYPE: RNA
<213> ORGANISM: Homo sapiens

<400> SEQUENCE: 8 ugucccccc ggcccagguu cugugauaca cuccgacucg ggucuggag cagucagugc      60 augacagaac uugggcccgg aaggacc                                       87

<210> SEQ ID NO 9
<211> LENGTH: 73
<212> TYPE: RNA
<213> ORGANISM: Mus musculus

<400> SEQUENCE: 9
ccgggccuag guucugugau acacuccgac ucgggcucug gagcagucag ugcaugacag    60
aacuugggcc cgg                                                      73

<210> SEQ ID NO 10

```
<211> LENGTH: 290
<212> TYPE: DNA
<213> ORGANISM: Homo sapiens

<400> SEQUENCE: 10
aaaacataaa tacatgaaaa tctgtctaag tcacccaatc tcccacaaaa caatctgcct    60
atacatcatt tccaagcacg attagcattt gaggtgaagt tctgttatac actcaggctg   120
tggctctctg aaagtcagtg catcacagaa ctttgtctcg aaagcttcct agcagctacc   180
cattttggga gtgggaggga agaatagacc ttttaaattc tttcagtgtg ccctaagct    240 gataaggtct ttctcaacag tcagcattta atgtgttaca aggtcaagcc              290

<210> SEQ ID NO 11
<211> LENGTH: 274
<212> TYPE: DNA
<213> ORGANISM: Mus musculus

<400> SEQUENCE: 11
agcagacacg aaaatctatc cctgccactc ctcctcccac agccagtctg cctacccacc    60
acttacaggc acccttagca tttgaggtga agttctgtta tacactcagg ctgtggctct   120
gaaagtcagt gcatcacaga actttgtctc gaaagctttc tagcagctgc ccatttgggg   180
agtgagaggg aagaatagat cttttcagtc ctttgaatat ggtcctaaga ttgtagggtc   240
tttttcaaga gtcagtattt aatgcatcac aagg                               274

<210> SEQ ID NO 12
<211> LENGTH: 1506
<212> TYPE: DNA
<213> ORGANISM: Homo sapiens

<400> SEQUENCE: 12
accttggggt catggttcag cagaggttac ataggagcaa atggttctca attttccagt    60
ttgattgaag tgcagagaaa atcccttag attgcaaaat aaaatagttg aactctctgt    120
cttcatgtgg aaggtttaga gcagttgtga gatgctgtta tgctgagaaa ccctgacttt   180
gttagtgttg gaaaaaagtc ttacaagtct ataatttaaa gatgtgatgg tggggagggg   240
aggatgggga agcttttat atatgcatac attacatacc tatatataaa cttgtggtat    300
aaccatagac catagctgca ggttaaccaa ttagttacta tcgtagagta atatatattc   360
agaataataa actcaagctg gagaaatgag tcctgataga ctgaaaattg agcaaatgga   420
agaagataca gtattgttta gatcagaatc attaaaaaat atttttgttt agtaagtttg   480
aagatttctg gcttttaggc cttttctatt ttgttccatt tattttttgca ggcaatcttt   540 tccatggagg gcagggtatc cattctttac catgggtgta cctgcttagg ttaaaaatca   600
taccaaggcc tcatacttcc aggtttcatg ttgcgtcttg ttgagggagg gagagcaggt   660
tacttggcaa ccatattgtc acctgtacct gtcacacatc ttgaaaaata aaacgataat   720
agaactagtg actaatttc ccttacagtt cctgcttggt cccacccact gaagtagctc    780
atcgtagtgc gggccgtatt agaggcagtg gggtacgtta gactcagatg gaaaagtatt   840
ctaggtgcca gtgttaggat gtcagttttta caaaataatg aagcaattag ctatgtgatt   900
gagagttatt gtttggggat gtgtgttgtg gttttgcttt ttttttttag actgtattaa   960
taaacataca acacaagctg gccttgtgtt gctggttcct attcagtatt tcctggggat  1020
tgtttgcttt ttaagtaaaa cacttctgac ccatagctca gtatgtctga attccagagg  1080
tcacatcagc atctttctgc tttgaaaact ctcacagctg tggctgcttc acttagatgc  1140
```

```
agtgagacac atagttggtg ttccgatttt cacatccttc catgtattta tcttgaagag    1200
ataagcacag aagagaaggt gctcactaac agaggtacat tactgcaatg ttctcttaac    1260
agttaaacaa gctgtttaca gtttaaactg ctgaatatta tttgagctat ttaaagctta    1320
ttatatttta gtatgaacta aatgaaggtt aaaacatgct taagaaaaat gcactgattt    1380
ctgcattatg tgtacagtat tggacaaagg attttattca ttttgttgca ttattttgaa    1440
tattgtcttt tcattttaat aaagttataa tacttattta tgataccatt aaaaaaaaaa    1500
aaaaaa                                                               1506

<210> SEQ ID NO 13
<211> LENGTH: 1394
<212> TYPE: DNA
<213> ORGANISM: Mus musculus

<400> SEQUENCE: 13 atatggggt catgattcaa cagaagttac atgggatgaa tggctcccag ttttccagtt      60
tgaggttcgt agaacaatgt caagtggcaa atgaagttg gtggactccg ccttaatgag     120
aaaggcttag agcagttatg aggtgctgtt atgctgggag tccctgatct atcagcatag    180
gagaaaaaag tatgatttaa agatgtgcta gggggaggga aaaatgggca acttttacat    240
ttgactacat tatataccta tgtataaaag tgcggtgtaa ccatagacca tagctgcagg    300
ataaccaatt agtcactctt agagtaatct gtattcagaa caattcaaac aagctggagg    360
aacagctcct gatagtgtga gaattgagca aatgggagaa agcaatattg ttagatcaga    420
ttataaattt gttaagttta aagattcctg gcatacaggc ctgctctata aatttgtttt    480
ccccttccct gccagcagtc ttctccatac acgacagggc gtgttctcca ccaggcctgt    540
aacatcttgt tgagatcatt tctatggccc aatacttgtc gctctggggt tttgtcttgt    600
tgaggagagg acagcagttt ctggaccatg ttatcacctg tgtgtgtctc atatcttgga    660
aattgacaga tttggtgaat aacttttcca tactattcct gcttttccca tccactgaaa    720
cagcctgttg tagcaagagg ctttcaagag tgcagtggag ttgcgctggc catcagtgtt    780
tggggtctga gtttgataga ctagtgcagc gatcagccat atgattgaga gctactttgg    840
ggatatatgg tacgttgttt ttgttttttta gacttaataa aggacaacac gagctggtct    900
tgtgttgctg gttcctattc agtatttcct ggggattgtt tgcttttaa gtgaaacact     960 tctgaccaat agcacagaac gtcttaatgc cagaggtcac ttcagcatct tcctgctttg    1020
aaaactcacg ctggctgctt cactgccctg agattcagtg agacacgcag tttgtgttca    1080 gttttacat cctctgattg tttatcttgt gcagataaac acaagagaa ggtgcttgct     1140 agcagggaca ctgctgccat gtcccaacaa gctgttcagt ttaaactgct gaatgacatt    1200
atttgagcta tttaaagctt actttagtat gaactaaatg aaggttaaaa catgctttag    1260
aaaaatgcac tgatctccgc actgtgtgta cagtattgga caaggatttt attcattttg    1320
ttgcattatt ttgaatattg tcttttcatt ttaataaagt tatattactt atttatgaaa    1380
aaaaaaaaaa aaaa                                                     1394

<210> SEQ ID NO 14
<211> LENGTH: 1361
<212> TYPE: DNA
<213> ORGANISM: Rattus norvegicus

<400> SEQUENCE: 14
```

```
atatggggtc atggttcaac agaagttaca tggaacggat ggctgccaag tttccaattt    60
gaggttcata gaacagtgtc aagtggcaac atgaagtggt ggactctgcc ttggtgagga   120
aggcatagag ccgttatgag gtgctgttgt gctgggagtc cctgacctat cagcatagga   180
agaaaaaagt atgatttaaa gatgtgctag agggacactt ttacatttga ctacattata   240
tacctatgta taaacgtgcg gtgtaaccat agaccatagc tgcaggataa ccaattagtc   300
actctagagt aatctatatt cagaacaatt caaacgagct ggaggcacag ctccagacag   360
tgtgaaaatt gagcaaacgg gagagagcag tactgttgat cagttataaa tgtagagatt   420
cctggcattc aggcctgcta tctagtttgt tttcttcccc ttccctgcca gcagtcttct   480
ccatacacga cagggcgtgc tcttcgccag gcctgtaacg tcttgttgaa atcgttctat   540
ggcctaatac ttgccgctct gggcgtttgt cttgagagga gaggacagcc gtttctggac   600
catgttatct atcacctgtg tatgtctctc ttggaaatgg acagaattgg tgacttttcc   660
atgctattcc tgcttttccc gtccactgaa gaggctttca agagtgcagt tgagtggtgc   720
tggccgtcag tgttgggtat aagttttata gaccagccca gtgattagcc atgattgaga   780
gttatcgtgg ggtgtatggg atgttgtttt gtttttgaga ctttaaagta caacacaagc   840
tggtcttgtg ttgttggttc ctattcagta tttcctgggg attgtttgct ttttaagtga   900
aacacttctg accaatagca cagaacgtct taatgccaga ggtcacttca gcatcttcct   960
gcttagaaaa ctcacagctg ctgcctcac tgccctgaga gtcagtgaga cgtgtagctt  1020
gtgttcaatt tttacatcct ctgattgttt atcttgtata gataagcaca agagaaggt  1080 gcttgctaac agagggacac cgctgccatg tcccaacaag ctgttcagtt taaactgctg  1140
aatgacatta tttgagctat ttaaagctta ttttagtat gaactaaatg aaggttaaaa  1200
catgctttag aaaatgcact gatctccgca ctgtgtgtac agtattggac aaaggatttg  1260
ttcattttgt tgcattattt tgaatattgt cttttcattt taataaagtt atattactta  1320
tttatgacac cgttaaaaaa aaaaaaaaaa aaaaaaaaaa a                      1361

<210> SEQ ID NO 15
<211> LENGTH: 120
<212> TYPE: DNA
<213> ORGANISM: Danio rerio

<400> SEQUENCE: 15
actaaccaag tgcacaaaag acttcttcgc tgctttgttg cagttttgct cgtaagtttg    60
agcaggttac aattaaatag cagttactgg gaaaaaaaaa aaaaaaaaa aaaaaaaaa   120

<210> SEQ ID NO 16
<211> LENGTH: 22
<212> TYPE: RNA
<213> ORGANISM: Artificial Sequence
<220> FEATURE:
<223> OTHER INFORMATION: Oligonucleotide

<400> SEQUENCE: 16
acaaaguucu gugaugcacu ga                                             22

<210> SEQ ID NO 17
<211> LENGTH: 22
<212> TYPE: RNA
```

```
<213> ORGANISM: Artificial Sequence
<220> FEATURE:
<223> OTHER INFORMATION: Oligonucleotide

<400> SEQUENCE: 17
acacacugcu gcgacguaau ga                                          22
```

THERAPEUTIC MICRO RNA TARGETS IN CHRONIC PULMONARY DISEASES

CROSS REFERENCE TO A RELATED APPLICATION

This application is a National Stage Application of International Application Number PCT/EP2013/060027, filed May 15, 2013; which claims the benefit of U.S. Provisional Application Ser. No. 61/650,005, filed May 22, 2012; both of which are incorporated herein by reference in their entirety.

The Sequence Listing for this application is labeled "SeqList-20Nov14.txt," which was created on Nov. 20, 2014, and is 10 KB. The entire content is incorporated herein by reference in its entirety.

The present invention relates to the identification of microRNAs of the miR-148 family that are involved in the pathogenesis of chronic pulmonary diseases. The present invention relates to micro RNA of the miR-148 family selected from miR-148a, miR-148b and miR-152 for use in the diagnosis, prognosis, prevention and/or therapy of a chronic pulmonary disease. The present invention further relates to miR-148 inhibitors, pharmaceutical compositions comprising such inhibitors, their use in preventing and/or treating chronic pulmonary diseases, and methods for preventing and/or treating chronic pulmonary diseases. The present invention further relates to transgenic, non-human mammals and methods for identifying modulators of miR-148 and methods for diagnosis and/or prognosis of chronic pulmonary diseases.

BACKGROUND OF THE INVENTION

Chronic obstructive lung diseases including cystic fibrosis (CF), chronic lung disease (CLD) of prematurity (also known as bronchopulmonary dysplasia; BPD), chronic bronchitis (CB), emphysema, and chronic obstructive pulmonary disease (COPD) belong to the most common chronic diseases in Europe and Northern America. CF is the most common fatal hereditary disease in white populations, CLD is a frequent health problem associated with premature birth, and cigarette smoke induced COPD with chronic bronchitis and/or emphysema has evolved as the fourth leading cause of death worldwide. All chronic obstructive lung diseases are accompanied by various degrees of airway mucus obstruction, goblet cell metaplasia and chronic inflammation of the respiratory tract and the formation of emphysema, i.e. disturbance in the development and/or destruction of alveoli, ultimately resulting in respiratory insufficiency.

Chronic obstructive pulmonary disease is a leading cause of death worldwide, but its pathogenesis is not well understood. Previous studies have shown that airway surface dehydration in β-epithelial Na+ channel (βENaC)-overexpressing mice caused a chronic lung disease with high neonatal pulmonary mortality and chronic bronchitis in adult survivors. Cystic fibrosis (CF) lung disease is the most common genetic form of chronic obstructive pulmonary disease (COPD) and is caused by mutations in the cystic fibrosis transmembrane conductance regulator (CFTR) gene, which encodes a protein that is a cAMP-dependent Cl$^-$ channel and regulates the epithelial Na$^+$ channel (ENaC). In CF airway epithelia, CFTR-mediated Cl$^-$ secretion is defective, and ENaC-mediated Na$^+$ absorption is increased. In vitro studies of primary human airway cultures suggested that these defects in vectorial ion transport resulted in airway surface liquid (ASL) volume depletion and adhesion of dehydrated mucus, which was predicted to impair normal ciliary function and efficient mucus clearance in CF airways. To further elucidate the role of ASL volume depletion in the in vivo pathogenesis of CF, a mouse model with airway-specific overexpression of ENaC was generated. In this mouse model, it was demonstrated (1) that overexpression of the β-subunit of ENaC (encoded by the Scnn1b gene) under control of the Clara cell secretory protein (CCSP) promoter was sufficient to increase airway Na$^+$ absorption in vivo, (2) that elevated airway Na$^+$ absorption caused ASL volume depletion and reduced mucus clearance, and (3) that deficient mucus clearance produced spontaneous lung disease sharing key features with CF and other forms of COPD, including substantial pulmonary mortality and airway mucus obstruction, goblet cell metaplasia, chronic neutrophilic inflammation, and impaired clearance of bacterial pathogens (Mall et al. 2004).

Together, the results from these in vitro and in vivo studies demonstrate that ASL volume depletion is a key mechanism in the pathogenesis of CF lung disease. Furthermore, cigarette smoke has recently been shown to decrease CFTR expression and cAMP-dependent Cl$^-$ secretion in vitro and in nasal respiratory epithelia of cigarette smokers in vivo. These data indicate that impaired ASL volume regulation may also be implicated in the pathogenesis of cigarette smoke-induced chronic bronchitis.

Mall et al. (2008) show that airway surface dehydration is sufficient to initiate persistent neutrophilic airway inflammation with chronic airways mucus obstruction and to cause emphysema in mice. These results suggest that deficient airway surface hydration plays a critical role in the pathogenesis of chronic obstructive pulmonary diseases of different etiologies and produced a mouse model to study the pathogenesis and test therapeutic interventions for chronic obstructive lung diseases in vivo.

So far, the in vivo pathogenesis of chronic obstructive lung diseases remains poorly understood, and the establishment of diagnostic and prognostic markers remains challenging.

Further, only limited therapies exist that target the symptoms of the disease rather than underlying mechanisms, such as bronchodilators (β-mimetics and anticholinergics), inhaled corticosteroids, mucolytics and antibiotics. Therefore, new diagnostic markers and new therapies targeting molecular mechanisms for effective prevention and treatment in chronic obstructive lung diseases are of high clinical and socioeconomic interest.

MicroRNAs (miRNAs) are a family of short regulatory RNAs that negatively control gene expression at the post-transcriptional level. Base pairing between the miRNA and the 3'-UTR of target mRNAs mediates specific translation inhibition and/or degradation of mRNA targets. miRNAs regulate numerous cellular processes as diverse as differentiation, proliferation and apoptosis. Moreover, cellular miRNAs are also important for the replication of pathogenic viruses (e.g., miR-122a facilitates replication of human hepatitis C), and small RNAs are also encoded by the genomes of several viruses to facilitate viral replication by suppressing cellular genes. Detection of differential expression of miRNAs in many cases has established the basis for miRNA functional analysis and the characterization of the important roles played by miRNAs. In addition, specific miRNA expression patterns can provide valuable diagnostic and prognostic indications in the context of human malignancies such as solid tumors and leukemias. miRNAs have also been identified as therapeutic targets and biomarkers, such as miR-208 as biomarker of myocardial injury (Ji et al., 2009).

There is a need for means and methods for the prevention of chronic pulmonary diseases, in particular of chronic obstructive pulmonary diseases, cystic fibrosis lung disease, and chronic lung disease of prematurity. There is a need for means and methods for the diagnosis, prognosis and therapy of said chronic pulmonary diseases.

SUMMARY OF THE INVENTION

According to the present invention this object is solved by micro RNA (miR-148) of the miR-148 family selected from miR-148a, miR-148b and miR-152 for use in the diagnosis, prognosis, prevention and/or therapy of a chronic pulmonary disease.

According to the present invention this object is solved by an inhibitor of a micro RNA of the miR-148 family, said micro RNA being selected from miR-148a, miR-148b and miR-152.

According to the present invention this object is solved by an inhibitor of a micro RNA of the miR-148 family according to the invention for use in preventing and/or treating a chronic pulmonary disease.

According to the present invention this object is solved by a pharmaceutical composition comprising at least one inhibitor of a micro RNA of the miR-148 family according to the present invention, optionally, a pharmaceutical excipient, and optionally, a further pulmonary medicament.

According to the present invention this object is solved by the pharmaceutical composition according to the present invention for use in preventing and/or treating a chronic pulmonary disease.

According to the present invention this object is solved by a method for the prevention and/or treatment of a chronic pulmonary disease, comprising administering to a patient at least one inhibitor of a micro RNA of the miR-148 family according to the invention or a pharmaceutical composition according to the invention.

According to the present invention this object is solved by a transgenic, non-human mammal, wherein the cells of said non-human mammal fail to express a functional micro RNA of the miR-148 family selected from miR-148a, miR-148b and miR-152 or wherein the cells of said non-human mammal comprise a coding region of a micro RNA of the miR-148 family selected from miR-148a, miR-148b and miR-152 under the control of a heterologous promoter active in the cells of said non-human mammal.

According to the present invention this object is solved by a method for identifying a modulator of micro RNA of the miR-148 family, said micro RNA being selected from miR-148a, miR-148b and miR-152, comprising:
 (a) contacting a cell with a candidate compound;
 (b) assessing miR-148 activity or expression; and
 (c) comparing the activity or expression in step (b) with the activity or expression in the absence of the candidate compound, wherein a difference between the measured activities or expression indicates that the candidate compound is a modulator of a micro RNA of the miR-148 family selected from miR-148a, miR-148b and miR-152.

According to the present invention this object is solved by a method for the diagnosis and/or prognosis of a chronic pulmonary disease comprising determining expression levels of micro RNA of the miR-148 family selected from miR-148a, miR-148b and miR-152 in patient specimen.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "at least 8 nucleotides, preferably 8 to 24" should be interpreted to include not only the explicitly recited values of 8 to 24, but also include individual values and sub-ranges within the indicated range. Thus, included in this numerical range are individual values such as 8, 9, 10, 11, 12, 13, 14, 15, 16, 17, 18, 19, 20, 21, 22, 23, 24 and sub-ranges such as from 10 to 15, from 10 to 20, from 10 to 24, from 15 to 24 and from 20 to 24, etc. As an illustration, a numerical range of "at least 20 nucleotides, preferably 20 to 105" should be interpreted to include not only the explicitly recited values of 20 to 105, but also include individual values and sub-ranges within the indicated range. Thus, included in this numerical range are individual values such as 20, 21, 22, 23, 24, 25, 26, 27, 28, 29, 20, . . . 100, 101, 102, 103, 104, 105 and sub-ranges such as from 20 to 85, from 20 to 50, from 25 to 50, from 30 to 50, and from 20 to 40, etc. This same principle applies to ranges reciting only one numerical value. Furthermore, such an interpretation should apply regardless of the breadth of the range or the characteristics being described.

miR-148 as Therapeutic Target and Marker of Chronic Pulmonary Diseases

MicroRNAs (miRNAs) belong to an important class of gene regulators involved in diverse biological and pathological processes, however, their role in chronic obstructive lung diseases is poorly understood. To study the potential role of miRNAs in the in vivo pathogenesis, the inventors used βENaC-overexpressing (βENaC-Tg) mice as a model of chronic obstructive lung disease and performed miRNA array analysis (miChip) in lung tissue from βENaC-Tg and wild-type (WT) mice. Differentially expressed miRNAs were validated by quantitative real-time PCR and their functional relevance was determined by bioinformatics analysis and in luciferase reporter assays. Tissue specific localization of candidate miRNAs was performed by in situ hybridization using locked nucleic acid (LNA)-modified DNA oligonucleotide probe. Direct functional studies were performed by blocking the miRNA expression in the lungs of βENaC-Tg mice by using antagomirs. The effects of antaogmir knockdown were studied by histological examination of lungs, pulmonary function testing using flexiVent system (SCIREQ) and analysis of inflammatory cells in bronchoalveolar lavage (BAL) fluid.

The inventors demonstrate that miR-148b is up-regulated in the lungs from βENaC-Tg mice compared to wild-type littermates. In situ hybridization showed that miR-148b is predominantly expressed and localized in the conducting airways. Bioinformatics analysis and luciferase assay in Hela cells suggest Mig-6 (mitogen inducible gene-6), a protein previously shown in normal lung development, as a potential target of miR-148b. The inventors' in vivo studies show that knockdown of miR-148b in the lung of βENaC-Tg mice results in reduced emphysema as measured by mean linear intercepts and pulmonary function testing. Further, analysis of differential cell counts in BAL showed decreased numbers of neutrophils in βENaC-Tg versus wild-type mice. The inventors show the upregulation of miR-148b in bronchial brushing of cystic fibrosis and COPD lung tissue from human. Furthermore, expression of miR-148b was shown by in situ localization in lung tissue section of human. Taken together, these results indicate that dysregulation of miR-148b expression plays an important role in the pathogenesis of chronic obstructive lung disease and that miR-148b represents a novel therapeutic target and biomarker.

microRNAs (miRNAs) are short (20-24 nt) non-coding RNAs that are involved in post-transcriptional regulation of gene expression in multicellular organisms by affecting both the stability and translation of mRNAs. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target mRNAs through imperfect base pairing with the miRNA and most commonly results in translational inhibition or destabilization of the target mRNA.

miR-148b is an intronic miRNA that is located within the Intron 1 of COPZ1 gene of mouse and human.

miR-148b belongs to the family of miR-148, which also comprises
miR-148a
miR-152.

The nucleotide sequences of the miR-148 members share a high sequence homology in their mature sequence and differ only in 2 nucleotides in their mature sequence.

miR-148 is a microRNA whose expression has been demonstrated in human, mouse, rat and zebrafish. miR-148 has also been predicted in chicken.

The mature miR-148b sequence is

[SEQ ID NO. 1]
5'-ucagugcaucacagaacuuugu-3'.

See also miRBase Accession No. MIMAT0000759 (hsa-miR-148b)

The pre-miRNA sequences for miR-148b for human and mouse are provided in SEQ ID NO. 4 and SEQ ID NO. 5, respectively.

The predicted pri-mRNA sequences for miR-148b for human and mouse are provided in SEQ ID NO. 10 and SEQ ID NO. 11, respectively.

The mature miR-148a sequence is

[SEQ ID NO. 2]
5'-ucagugcacuacagaacuuugu-3'.

See also miRBase Accession No. MIMAT0000243.

The mature miR-148a sequence has about 90% sequence identity to the mature miR-148b sequence, it differs in 2 nucleotides.

The pre-miRNA sequences for miR-148a for human and mouse are provided in SEQ ID NO. 6 and SEQ ID NO. 7, respectively.

The mature miR-152 sequence is

[SEQ ID NO. 3]
5'-ucagugcaugacagaacuugg-3'.

See also miRBase Accession No. MIMAT0000438.

The mature miR-152 sequence has about 90% sequence identity to the mature miR-148b sequence, it differs in one nucleotide and is one nucleotide shorter.

The pre-miRNA sequences for miR-152 for human and mouse are provided in SEQ ID NO. 8 and SEQ ID NO. 9, respectively.

Sequences:

```
1) miR-148b
Homo sapiens primary miR-148b sequence region predicted from Intron
1 of COPZ1 gene
Pri-miR-148b (human)
                                                           SEQ ID NO. 10
AAAACATAAATACATGAAAATCTGTCTAAGTCACCCAATCTCCCACAAAACAATCTGCCTATACATCATT
TCCAAGCACGATTAGCATTTGAGGTGAAGTTCTGTTATACACTCAGGCTGTGGCTCTCTGAAAGTCAGTG
CATCACAGAACTTTGTCTCGAAAGCTTTCTAGCAGCTACCCATTTTGGGAGTGGGAGGGAAGAATAGACC
TTTTAAATTCTTTCAGTGTGGCCCTAAGCTGATAAGGTCTTTCTCAACAGTCAGCATTTAATGTGTTACA
AGGTCAAGCC Homo sapiens miR-148b stem-loop (Pre-hsa-miR-148b)
hsa-mir-148b (miRBase Accession No.MI0000811)
                                                           SEQ ID NO. 4
CAAGCACGAUUAGCAUUUGAGGUGAAGUUCUGUUAUACACUCAGGCUGUGGCUCUCUGAAAGUCAGUGCA
UCACAGAACUUUGUCUCGAAAGCUUUCUA
```

-continued

*Homo sapiens* miR-148b mature sequence (hsa-miR-148b)
hsa-miR-148b-3p (miRBase Accession No.MIMAT0000759)
SEQ ID NO. 1

UCAGUGCAUCACAGAACUUUGU

*Mus musculus* primary miR-148b sequence region predicted from Intron 1
of Copz1 gene
Pri-miR-148b (mouse)
SEQ ID NO. 11

AGCAGACACGAAAATCTATCCCTGCCACTCCTCCTCCCACAGCCAGTCTGCCTACCCACCACTTACAGGC
ACCCTTAGCATTTGAGGTGAAGTTCTGTTATACACTCAGGCTGTGGCTCTGAAAGTCAGTGCATCACAGA
ACTTTGTCTCGAAAGCTTTCTAGCAGCTGCCCATTTGGGGAGTGAGAGGGAAGAATAGATCTTTTCAGTC
CTTTGAATATGGTCCTAAGATTGTAGGGTCTTTTTCAAGAGTCAGTATTTAATGCATCACAAGG

*Mus musculus* miR-148b stem-loop (Pre-mmu-miR-148b)
mmu-mir-148b (miRBase Accession No.MI0000617)
SEQ ID NO. 5

CAGGCACCCUUAGCAUUUGAGGUGAAGUUCUGUUAUACACUCAGGCUGUGGCUCUGAAAGUCAGUGCAUC
ACAGAACUUUGUCUCGAAAGCUUUCUA

*Mus musculus* miR-148b mature sequence (mmu-miR-148b)
mmu-miR-148b-3p (miRBase Accession No. MIMAT0000580)
SEQ ID NO. 1

UCAGUGCAUCACAGAACUUUGU 2) miR-148a
*Homo sapiens* miR-148a stem-loop (Pre-hsa-miR-148a)
hsa-mir-148a (miRBase Accession No. MI0000253)
SEQ ID NO. 6

GAGGCAAAGUUCUGAGACACUCCGACUCUGAGUAUGAUAGAAGUCAGUGCACUACAGAACUUUGUCUC

*Homo sapiens* miR-148a mature sequence (hsa-miR-148a)
hsa-miR-148a-3p (miRBase Accession No. MIMAT0000243)
SEQ ID NO. 2 ucagugcacuacagaacuuugu

*Mus musculus* miR-148a stem-loop (Pre-mmu-miR-148a)
mmu-mir-148a (miRBase Accession No. MI0000550)
SEQ ID NO. 7

AGCCAGUUUGGUCUUUUGAGACAAAGUUCUGAGACACUCCGACUCUGAGUAUGAUAGAAGUCAGUGCAC
UACAGAACUUUGUCUCUAGAGGCUGUGGUC

*Mus musculus* miR-148a mature sequence (mmu-miR-148ab)
mmu-miR-148a-3p (miRBase Accession No. MIMAT0000516)
SEQ ID NO. 2 ucagugcacuacagaacuuugu 3) miR-152
*Homo sapiens* miR-152 stem-loop (Pre-hsa-miR-152)
hsa-mir-152 (miRBase Accession No. MI0000462)
SEQ ID NO. 8

UGUCCCCCCCGGCCCAGGUUCUGUGAUACACUCCGACUCGGGCUCUGGAGCAGUCAGUGCAUGACAGAAC
UUGGGCCCGGAAGGACC

Homo sapiens miR-152 mature sequence (hsa-miR-152)
hsa-miR-152-3p (miRBase Accession No. MIMAT0000438)
SEQ ID NO. 3 ucagugcaugacagaacuugg

*Mus musculus* miR-152 stem-loop (Pre-mmu-miR-152)
mmu-mir-152 (miRBase Accession No. MI0000174)
SEQ ID NO. 9

CCGGGCCUAGGUUCUGUGAUACACUCCGACUCGGGCUCUGGAGCAGUCAGUGCAUGACAGAACUUGGGCC
CGG

*Mus musculus* miR-148a mature sequence (mmu-miR-152)
mmu-miR-152-3p (miRBase Accession No. MIMAT0000162)
SEQ ID NO. 3 ucagugcaugacagaacuugg

Using the TargetScan, PicTar and DIANA-microT algorithms for the prediction/identification of miRNA targets (Crimson et al., 2007, Krek et al., 2005, Maragkakis et al., 200), the inventors identified potential targets of miR-148b associated with lung phenotype (see FIG. 3A) comprising:
phosphatase and tensin homolog (PTEN);
sphingosine-1-phosphate receptor 1 (S1PR1)
ERBB receptor feedback inhibitor 1 (ERRFI 1) (also called Mig-6)
fibrillin 1 (FBN1)
mesenchyme homeobox 2 (MEOX2)
cullin-associated and neddylation-dissociated 1 (CAND1).

Mig-6 3' UTR sequences from human, mouse, rat, and zebrafish are provided in SEQ ID NO. 12, SEQ ID NO. 13, SEQ ID NO. 14, SEQ ID NO. 15, respectively.

```
Homo sapiens (Human) MIG-6 (ERRFI1) 3'UTR sequence
ACCESSION NM_018948 (starting from nucleotide 1639 of mRNA)
                                                    SEQ ID NO. 12
ACCTTGGGGTCATGGTTCAGCAGAGGTTACATAGGAGCAAATGGTTCTCAATTTTCCAGT
TTGATTGAAGTGCAGAGAAAAATCCCTTAGATTGCAAAATAAAATAGTTGAACTCTCTGT
CTTCATGTGGAAGGTTTAGAGCAGTTGTGAGATGCTGTTATGCTGAGAAACCCTGACTTT
GTTAGTGTTGGAAAAAAGTCTTACAAGTCTATAATTTAAAGATGTGATGGTGGGGAGGGG
AGGATGGGGAAGCTTTTTATATATGCATACATTACATACCTATATATAAACTTGTGGTAT
AACCATAGACCATAGCTGCAGGTTAACCAATTAGTTACTATCGTAGAGTAATATATATTC
AGAATAATAAACTCAAGCTGGAGAAATGAGTCCTGATAGACTGAAAATTGAGCAAATGGA
AGAAGATACAGTATTGTTTAGATCAGAATCATTAAAAAATATTTTTGTTTAGTAAGTTTG
AAGATTTCTGGCTTTTAGGCCTTTTCTATTTTGTTCCATTTATTTTTGCAGGCAATCTTT
TCCATGGAGGGCAGGGTATCCATTCTTTACCATGGGTGTACCTGCTTAGGTTAAAAATCA
TACCAAGGCCTCATACTTCCAGGTTTCATGTTGCGTCTTGTTGAGGGAGGGAGAGCAGGT
TACTTGGCAACCATATTGTCACCTGTACCTGTCACACATCTTGAAAAATAAAACGATAAT
AGAACTAGTGACTAATTTTCCCTTACAGTTCCTGCTTGGTCCCACCCACTGAAGTAGCTC
ATCGTAGTGCGGGCCGTATTAGAGGCAGTGGGGTACGTTAGACTCAGATGGAAAGTATT
CTAGGTGCCAGTGTTAGGATGTCAGTTTTACAAAATAATGAAGCAATTAGCTATGTGATT
GAGAGTTATTGTTTGGGGATGTGTGTTGTGGTTTTGCTTTTTTTTTTAGACTGTATTAA
TAAACATACAACACAAGCTGGCCTTGTGTTGCTGGTTCCTATTCAGTATTTCCTGGGGAT
TGTTTGCTTTTTAAGTAAAACACTTCTGACCCATAGCTCAGTATGTCTGAATTCCAGAGG
TCACATCAGCATCTTTCTGCTTTGAAAACTCTCACAGCTGTGGCTGCTTCACTTAGATGC
AGTGAGACACATAGTTGGTGTTCCGATTTTCACATCCTTCCATGTATTTATCTTGAAGAG
ATAAGCACAGAAGAGAAGGTGCTCACTAACAGAGGTACATTACTGCAATGTTCTCTTAAC
AGTTAAACAAGCTGTTTACAGTTTAAACTGCTGAATATTATTTGAGCTATTTAAAGCTTA
TTATATTTTAGTATGAACTAAATGAAGGTTAAAACATGCTTAAGAAAAATGCACTGATTT
CTGCATTATGTGTACAGTATTGGACAAAGGATTTTATTCATTTTGTTGCATTATTTTGAA
TATTGTCTTTTCATTTTAATAAAGTTATAATACTTATTTATGATACCATTAAAAAAAAAA
AAAAAA Mus musculus (Mouse) Mig-6 (Errfi1) 3'UTR sequence
ACCESSION NM_133753 (starting from nucleotide 1641 of mRNA)
                                                    SEQ ID NO. 13
ATATGGGGGTCATGATTCAACAGAAGTTACATGGGATGAATGGCTCCCAGTTTTCCAGTT
TGAGGTTCGTAGAACAATGTCAAGTGGCAAAATGAAGTTGGTGGACTCCGCCTTAATGAG
AAAGGCTTAGAGCAGTTATGAGGTGCTGTTATGCTGGGAGTCCCTGATCTATCAGCATAG
GAGAAAAAAGTATGATTTAAAGATGTGCTAGGGGGAGGGAAAAATGGGCAACTTTTACAT
TTGACTACATTATATACCTATGTATAAAAGTGCGGTGTAACCATAGACCATAGCTGCAGG
ATAACCAATTAGTCACTCTTAGAGTAATCTGTATTCAGAACAATTCAAACAAGCTGGAGG
AACAGCTCCTGATAGTGTGAGAATTGAGCAAATGGGAGAAAGCAATATTGTTAGATCAGA
TTATAAATTTGTTAAGTTTAAAGATTCCTGGCATACAGGCCTGCTCTATAAATTTGTTTT
CCCCTTCCCTGCCAGCAGTCTTCTCCATACACGACAGGGCGTGTTCTCCACCAGGCCTGT
AACATCTTGTTGAGATCATTTCTATGGCCCAATACTTGTCGCTCTGGGGTTTTGTCTTGT
TGAGGAGAGGACAGCAGTTTCTGGACCATGTTATCACCTGTGTGTGTCTCATATCTTGGA
AATTGACAGATTTGGTGAATAACTTTTCCATACTATTCCTGCTTTTCCCATCCACTGAAA
CAGCCTGTTGTAGCAAGAGGCTTTCAAGAGTGCAGTGGAGTTGCGCTGGCCATCAGTGTT
TGGGGTCTGAGTTTGATAGACTAGTGCAGCGATCAGCCATATGATTGAGAGCTACTTTGG
GGATATATGGTACGTTGTTTTGTTTTTTAGACTTAATAAAGGACAACACGAGCTGGTCT
TGTGTTGCTGGTTCCTATTCAGTATTTCCTGGGGATTGTTTGCTTTTTAAGTGAAACACT
TCTGACCAATAGCACAGAACGTCTTAATGCCAGAGGTCACTTCAGCATCTTCCTGCTTTG
AAAACTCACGCTGGCTGCTTCACTGCCCTGAGATTCAGTGAGACACGCAGTTTGTGTTCA
GTTTTTACATCCTCTGATTGTTTATCTTGTGCAGATAAACACAAAGAGAAGGTGCTTGCT
AGCAGGGACACTGCTGCCATGTCCCAACAAGCTGTTCAGTTTAAACTGCTGAATGACATT
ATTTGAGCTATTTAAAGCTTACTTTAGTATGAACTAAATGAAGGTTAAAACATGCTTTAG
AAAAATGCACTGATCTCCGCACTGTGTGTACAGTATTGGACAAAGGATTTATTCATTTTG
TTGCATTATTTTGAATATTGTCTTTTCATTTTAATAAAGTTATATTACTTATTTATGAAA
AAAAAAAAAAAAAA Rattus norvegicus (Rat) Mig-6 (Errfi1) 3'UTR sequence
ACCESSION NM_001014071 (starting from nucleotide 1647 of mRNA)
                                                    SEQ ID NO. 14
ATATGGGGTCATGGTTCAACAGAAGTTACATGGAACGGATGGCTGCCAAGTTTCCAATTT
GAGGTTCATAGAACAGTGTCAAGTGGCAACATGAAGTGGTGGACTCTGCCTTGGTGAGGA
AGGCATAGAGCCGTTATGAGGTGCTGTTGTGCTGGGAGTCCCTGACCTATCAGCATAGGA
AGAAAAAGTATGATTTAAAGATGTGCTAGAGGGACACTTTTACATTTGACTACATTATA
TACCTATGTATAAACGTGCGGTGTAACCATAGACCATAGCTGCAGGATAACCAATTAGTC
ACTCTAGAGTAATCTATATTCAGAACAATTCAAACGAGCTGGAGGCACAGCTCCAGACAG
TGTGAAAATTGAGCAAACGGGAGAGAGCAGTACTGTTGATCAGTTATAAATGTAGAGATT
CCTGGCATTCAGGCCTGCTATCTAGTTTGTTTTCTTCCCCTTCCCTGCCAGCAGTCTTCT
```

```
                                    -continued
CCATACACGACAGGGCGTGCTCTTCGCCAGGCCTGTAACGTCTTGTTGAAATCGTTCTAT
GGCCTAATACTTGCCGCTCTGGGCGTTTGTCTTGAGAGGAGAGGACAGCCGTTTCTGGAC
CATGTTATCTATCACCTGTGTATGTCTCTCTTGGAAATGGACAGAATTGGTGACTTTTCC
ATGCTATTCCTGCTTTTCCCGTCCACTGAAGAGGCTTTCAAGAGTGCAGTTGAGTGGTGC
TGGCCGTCAGTGTTGGGTATAAGTTTTATAGACCAGCCCAGTGATTAGCCATGATTGAGA
GTTATCGTGGGGTGTATGGGATGTTGTTTTGTTTTTGAGACTTTAAAGTACAACACAAGC
TGGTCTTGTGTTGTTGGTTCCTATTCAGTATTTCCTGGGGATTGTTTGCTTTTTAAGTGA
AACACTTCTGACCAATAGCACAGAACGTCTTAATGCCAGAGGTCACTTCAGCATCTTCCT
GCTTAGAAAACTCACAGCTGGCTGCCTCACTGCCCTGAGAGTCAGTGAGACGTGTAGCTT
GTGTTCAATTTTTACATCCTCTGATTGTTTATCTTGTATAGATAAGCACAAAGAGAAGGT
GCTTGCTAACGAGGGACACCGCTGCCATGTCCCAACAAGCTGTTCAGTTTAAACTGCTG
AATGACATTATTTGAGCTATTTAAAGCTTATTTTTAGTATGAACTAAATGAAGGTTAAAA
CATGCTTTAGAAAATGCACTGATCTCCGCACTGTGTGTACAGTATTGGACAAAGGATTTG
TTCATTTTGTTGCATTATTTTGAATATTGTCTTTTCATTTTAATAAAGTTATATTACTTA
TTTATGACACCGTTAAAAAAAAAAAAAAAAAAAAAAAAAAAAA Danio rerio (Zebrafish) Mig-6 (Errfi1) 3'UTR sequence
ACCESSION NM_001083570 (starting from nucleotide 1528 of mRNA)
                                                            SEQ ID NO. 15
ACTAACCAAGTGCACAAAAGACTTCTTCGCTGCTTTGTTGCAGTTTTGCTCGTAAGTTTG
AGCAGGTTACAATTAAATAGCAGTTACTGGGAAAAAAAAAAAAAAAAAAAAAAAAAAAA
```

As described above, the present invention provides micro RNA of the miR-148 family selected from miR-148a, miR-148b and miR-152 for use in the diagnosis, prognosis, prevention and/or therapy of a chronic pulmonary disease.

The present invention provides micro RNA of the miR-148 family selected from miR-148a, miR-148b and miR-152 as diagnosis and/or prognosis marker of a chronic pulmonary disease.

Thereby, at least one of the members of the miR-148 family is utilized, preferably miR-148b. In some embodiments, one, two or all members of the miR-148 family can be utilized, namely used in the diagnosis, prognosis, prevention and/or therapy of a chronic pulmonary disease.

Preferably, the chronic pulmonary disease is selected from chronic obstructive pulmonary disease (COPD), chronic bronchitis (CB), emphysema, cystic fibrosis (CF) lung disease, chronic lung disease (CLD) associated with premature birth, and other acquired and genetically determined forms of chronic lung diseases.

In one embodiment, the use comprises determining miR-148 expression levels in patient specimen.

Preferably, miR-148b expression levels in patient specimen are determined.

The patient specimen comprises preferably sputum, bronchoalveolar lavage fluid, blood, urine and lung tissue.

Preferably, the diagnosis and/or prognosis of said chronic pulmonary disease comprises said determining miR-148 expression levels in patient specimen.

An upregulation of miR-148 expression or an increased miR-148 expression (preferably upregulation of miR-148b expression or an increased miR-148b expression) compared to a normal or control sample is indicative of a chronic pulmonary disease.

In one embodiment, miR-148 expression levels of the patient sample or specimens are determined at different time points, such as at the time of diagnosing a chronic pulmonary disease or at the time of beginning a therapy or during therapy. A change in the miR-148 expression levels at these different time points, when compared to the miR-148 expression levels of the first measured time point, can be an indication of the progression or advance of the chronic pulmonary disease in the patient or can be an indication whether the therapy is effective or not.

In one embodiment, miR-148 expression levels of the patient sample or specimens are determined for (early) diagnosing a chronic pulmonary disease, preferably for confirming such a diagnosis which was performed using other means or before such diagnosis using other means is established, performed or possible.

Preferably, miR-148 expression levels of the patient sample or specimens are determined when a chronic pulmonary disease is suspected on the basis of non-specific clinical symptoms, such as cough, or diagnostic findings comprising impaired lung function or morphological changes in chest X-ray, CT or MRI scans.

Diagnosis of COPD is performed on basis of clinical symptoms (cough), impaired lung function and morphological changes, i.e. bronchitis, mucus plugging, bronchiectasis, emphysema as determined from chest X-ray, chest CT scan or chest MRI scan. In CF as genetically determined form of COPD, diagnosis is confirmed by genetic testing, i.e. identification of mutations in the CFTR gene. However, cough is relatively non-specific symptom, so diagnosis at early stage remains difficult and that is where a new and specific diagnostic marker is of help.

In one embodiment, miR-148 expression and/or activity and/or function are inhibited.

Preferably, miR-148b expression and/or activity and/or function are inhibited.

Preferably, the prevention and/or therapy of said chronic pulmonary disease comprises inhibiting miR-148 expression and/or activity and/or function, preferably inhibiting miR-148b expression and/or activity and/or function.

miRNA activity and/or expression and/or function can be inhibited in different ways, such as by using antisense oligonucleotides or oligonucleotides that are complementary to the nucleotide sequence of the target miRNA as inhibitors, which are preferably chemically modified. DNA vector systems or viral vector systems can be used that express the antisense or complementary oligonucleotides; liposomes delivering said antisense or complementary oligonucleotides can be utilized.

Preventive treatment is performed by initiating therapy prior to the onset of chronic and irreversible lung changes such as bronchiectasis, airway remodelling and emphysema. This is facilitated by early diagnosis using the new specific diagnostic marker according to the invention.

Treatment preferably means initiation of therapy after the diagnosis has been established, which in general also implicates the development of chronic lung lesions including e.g. bronchiectasis, airway remodelling and emphysema.

For both, treatment is preferably performed by inhalation therapy (aerosol, dry powder, solution) with adequate device—as discussed herein, for details see below. And potentially other forms of application.

Inhibitors of miR-148

As described above, the present invention provides inhibitors of micro RNA of the miR-148 family, said micro RNA of the miR-148 family being selected from miR-148a, miR-148b and miR-152.

The inhibitors of the present invention are preferably directed at the mature sequence(s) of the miR-148, but can also be directed at the pre-miR 148 sequence(s), or even the pri-miR 148 sequence(s).

An inhibitor of the present invention is directed at at least one of the members of the miR-148 family, preferably miR-148b. In some embodiments, an inhibitor of the present invention is directed at one, two or all members of the miR-148 family.

Inhibitors of miRNAs can take the form of "antagomirs," short, chemically-engineered single-stranded oligonucleotides complementary to miRNAs that block the function of miRNAs (Krützfeldt et al., 2005). Other approaches include inhibition of miRNAs with antisense 2'-O-methyl (2'-OMe) oligoribonucleotides and small interfering double-stranded RNAs (siRNAs) engineered with certain "drug-like" properties (chemical modifications for stability; cholesterol conjugation for delivery) (Krützfeldt et al., 2005).

"Antagomirs" are one of a novel class of chemically engineered oligonucleotides. Antagomirs are used to silence endogenous microRNA. An antagomir is a small synthetic RNA that is (perfectly) complementary to the specific miRNA target with either mispairing at the cleavage site of Ago2 or some sort of base modification to inhibit Ago2 cleavage. Usually, antagomirs have some sort of modification, such as 2' methoxy or 2' methyl groups and phosphothioates, to make it more resistant to degradation. It is unclear how antagomirization (the process by which an antagomir inhibits miRNA activity) operates, but it is believed to inhibit by irreversibly binding the miRNA. Antagomirs are now used as a method to constitutively inhibit the activity of specific miRNAs. For example, antagomirs against miR-21 have been successfully used to inhibit fibrosis of heart and lung.

In a preferred embodiment, the inhibitor according to the invention comprises or consists of an oligonucleotide selected from (i) an antisense oligonucleotide to the nucleotide sequence of a micro RNA of the miR-148 family selected from miR-148a, miR-148b and miR-152;

(ii) a nucleic acid sequence that is complementary to at least 8 contiguous nucleotides of the nucleotide sequence of a micro RNA of the miR-148 family selected from miR-148a, miR-148b and miR-152.

Preferably, the oligonucleotide is an antisense oligonucleotide to the nucleotide sequence of miR-148b or a nucleic acid sequence that is complementary to at least 8 contiguous nucleotides of the nucleotide sequence of miR-148b.

In embodiment (ii), the oligonucleotide comprises or has a nucleic acid sequence that is complementary to at least 8 contiguous nucleotides of the nucleotide sequence of a micro RNA of the miR-148 family selected from miR-148a, miR-148b and miR-152, preferably complementary to at least 8 contiguous nucleotides of the mature nucleotide sequence of a micro RNA of the miR-148 family selected from miR-148a, miR-148b and miR-152, such as complementary to 8 to 24 contiguous nucleotides, such as 8, 9, 10, 11, 12, 13, 14, 15, 16, 17, 18, 19, 20, 21, 22, 23, 24, of the mature sequence of a micro RNA of the miR-148 family selected from miR-148a, miR-148b and miR-152.

The oligonucleotide can also comprise or have a nucleic acid sequence that is complementary to (or complementary to at least 8 contiguous nucleotides of) a sequence having at least 80% sequence identity, preferably at least 85% or at least 90% or at least 95% sequence identity to a nucleotide sequence of the mature nucleotide sequence of a micro RNA of the miR-148 family selected from miR-148a, miR-148b and miR-152.

In one embodiment, the oligonucleotide comprises or has a nucleic acid sequence that is complementary to at least 20 contiguous nucleotides of the pre-miR nucleotide sequence of a micro RNA of the miR-148 family selected from miR-148a, miR-148b and miR-152, such as complementary to 20 to 105 contiguous nucleotides, such as 20, 21, 22, 23, 24, 25, 26, 27, 28, 29, 20, . . . 100, 101, 102, 103, 104, 105 of the pre-miR nucleotide sequence of a micro RNA of the miR-148 family selected from miR-148a, miR-148b and miR-152, preferably complementary to 20 to 50 contiguous nucleotides.

The oligonucleotide can also comprise or have a nucleic acid sequence that is complementary to (or complementary to at least 10 contiguous nucleotides of) a sequence having at least 80% sequence identity, preferably at least 85% or at least 90% or at least 95% sequence identity to a nucleotide sequence of the pre-miR nucleotide sequence of a micro RNA of the miR-148 family selected from miR-148a, miR-148b and miR-152.

The oligonucleotide sequence is 8 to 105 nucleotides in length, such as 8 to 24, 10 to 15, 10 to 20, 10 to 24, 15 to 24, 20 to 24, 20 to 25, 20 to 30, about 20, about 21, about 22, about 23, about 24, about 25, 20 to 40, or 20 to 105, 20 to 85, 20 to 50, 25 to 50, 30 to 50.

The oligonucleotide can have the same nucleotide length as the target miRNA sequence. In some embodiments, the oligonucleotide has a shorter or longer nucleotide sequence than the target miRNA sequence.

Preferably, the oligonucleotide comprises RNA, LNA or combinations thereof.

Preferably, the oligonucleotide is single stranded.

In a preferred embodiment, the oligonucleotide comprises or has (i) a sequence complementary to
the mature miR-148b nucleotide sequence

[SEQ ID NO. 1]
5'-ucagugcaucacagaacuuugu-3'.

the mature miR-148a nucleotide sequence,

[SEQ ID NO. 2]
5'-ucagugcacuacagaacuuugu-3'.

the mature miR-152 nucleotide sequence

[SEQ ID NO. 3]
5'-ucagugcaugacagaacuugg-3'.

or a sequence having at least 80% sequence identity, preferably at least 85% or at least 90% or at least 95% sequence identity to a nucleotide sequence selected from SEQ ID NOs. 1 to 3, or (ii) a sequence complementary to at least 8 contiguous nucleotides of a nucleotide sequence selected from SEQ ID NOs. 1 to 3 or a sequence having at least 80% sequence identity, preferably at least 85% or at least 90% or at least 95% sequence identity to a nucleotide sequence selected from SEQ ID NOs. 1 to 3.

The oligonucleotide sequence is preferably 8 to 24 nucleotides in length, such as 8 to 24, 10 to 15, 10 to 20, 10 to 24, 15 to 24, about 20, about 21, about 22, about 23, about 24, or is 8 to 40 nucleotides in length, such as 20 to 30, 20 to 40.

In a preferred embodiment, the oligonucleotide comprises or has (i) a sequence complementary to a nucleotide sequence selected from a pre-miR 148 nucleotide sequence of SEQ ID NOs. 4 to 9 or a sequence having at least 80% sequence identity, preferably at least 85% or at least 90% or at least 95% sequence identity to a nucleotide sequence selected from SEQ ID NOs. 4 to 9, or (ii) a sequence complementary to at least 20 contiguous nucleotides of a nucleotide sequence selected from SEQ ID NOs. 4 to 9 or a sequence having at least 80% sequence identity, preferably at least 85% or at least 90% or at least 95% sequence identity to a nucleotide sequence selected from SEQ ID NOs. 4 to 9.

The oligonucleotide sequence is preferably 20 to 105 nucleotides in length, such as 20 to 105, to 85, 20 to 50, 25 to 50, 30 to 50.

In a preferred embodiment, the inhibitor according to the invention comprises or consists of an oligonucleotide comprising or having the nucleotide sequence:

[SEQ ID NO. 16]
5'-acaaaguucugugaugcacuga-3'

Preferably, the oligonucleotides as defined herein comprise modifications to make it more resistant to degradation, such as by RNases, and/or inhibit cleavage, such as by Ago.

Preferably, the oligonucleotide comprises at least one 2'-O-modified nucleotide, such as a 2'-O-methyl modified nucleotide(s) or 2'-O-methoxy modified nucleotide(s).

In one embodiment, at least two, three, four and up to all nucleotides/bases have 2'-O-modifications, such as 2'-O-methyl or 2'-O-methoxy modification(s).

Preferably, the oligonucleotide comprises phosphorothioate linkage(s).

In one embodiment, at least two, three, four and up to all nucleotides have phoshorothioate linkages.

In one embodiment, the nucleotide(s) at the 5' end and/or the 3' end have phosphorothioate linkages.

In one embodiment, the first two nucleotides (5' end) and the last four nucleotides (3' end) have phoshorothioate linkages.

Preferably, the oligonucleotides as defined herein comprise are conjugated, such as to allow cell delivery.

In one embodiment, the oligonucleotide is conjugated near or at an end, such as near or at the 3' end, preferably with hydrophobic group(s) or moiety(ies), such as cholesterol.

In one embodiment, the inhibitor comprises a cellular delivery construct or carrier for the oligonucleotide, such as an expression vector, a virus or parts thereof, or liposome.

In one embodiment, the inhibitor is an antagomir of miR-148b.

Preferably, the inhibitor according to the invention is an oligonucleotide comprising or having the sequence:

[SEQ ID NO. 16]
5'-acaaaguucugugaugcacuga-3' and preferably having the following modifications at least two, preferably all nucleotides/bases have 2'-O-methyl modifications, the nucleotides at the ends, preferably the first two nucleotides/bases and the last four nucleotides/bases have phoshorothioate linkages, and the 3' end is conjugated, preferably a cholesterol molecule is conjugated at the 3' end.

As described above, the present invention provides a pharmaceutical composition comprising at least one inhibitor of a micro RNA of the miR-148 family according to the invention, optionally, a pharmaceutical excipient, optionally, a further pulmonary medicament.

Preferably, the pharmaceutical composition comprises at least one inhibitor of miR-148b according to the invention, optionally, a pharmaceutical excipient, optionally, a further pulmonary medicament.

In some embodiment, the pharmaceutical composition comprises two, three or more inhibitors of a micro RNA of the miR-148 family according to the invention.

miR-148 Inhibitors and Pharmaceutical Compositions for Use in Preventing and/or Treating Chronic Pulmonary Diseases As described above, the present invention provides miR-148 inhibitors (preferably miR-148b inhibitors) for use in preventing and/or treating chronic pulmonary diseases.

As described above, the present invention provides pharmaceutical compositions comprising the miR-148 inhibitors for use in preventing and/or treating chronic pulmonary diseases.

Preferably, the chronic pulmonary disease is selected from chronic obstructive pulmonary disease (COPD), chronic bronchitis (CB), emphysema, cystic fibrosis (CF) lung disease, chronic lung disease (CLD) associated with premature birth, and other acquired and genetically determined forms of chronic lung diseases.

Preferably, the inhibitor(s) or pharmaceutical composition(s) is (are) administered to a subject in need thereof by inhalation, intranasal, intravenous, oral, transdermal, sustained release, controlled release, delayed release, suppository, or sublingual administration.

Administration by inhalation is preferably as aerosol, dry powder or solution, preferably using a spacer, metered dose inhaler (MDI) or nebulizer.

In one embodiment, the inhibitor(s) or pharmaceutical composition(s) is (are) administered to a subject in need thereof in combination with a second pulmonary therapy.

Said second therapy preferably selected from a therapy or treatment with bronchodilators, such as short and long-acting b2-agonists, anticholinergic agents, inhaled corticosteroids (ICS), or inhaled mucolytics, such as DNAse, hypertonic saline.

Methods for Preventing and/or Treating Chronic Pulmonary Diseases

As described above, the present invention provides method(s) for the prevention and/or treatment of a chronic pulmonary disease.

The methods of the invention comprise administering to a patient at least one inhibitor of a micro RNA of the miR-148 family according to the invention or a pharmaceutical composition according to the invention.

The chronic pulmonary disease is preferably selected from chronic obstructive pulmonary disease (COPD), chronic bronchitis (CB), emphysema, cystic fibrosis (CF) lung disease, chronic lung disease (CLD) associated with premature birth, and other acquired and genetically determined forms of chronic lung diseases.

Preferably, the inhibitor(s) or pharmaceutical composition(s) is (are) administered to a subject in need thereof by inhalation, intranasal, intravenous, oral, transdermal, sustained release, controlled release, delayed release, suppository, or sublingual administration.

Administration by inhalation is preferably as aerosol, dry powder or solution, preferably using a spacer, metered dose inhaler (MDI) or nebulizer.

In one embodiment, the inhibitor(s) or pharmaceutical composition(s) is (are) administered to a subject in need thereof in combination with a second pulmonary therapy.

Said second therapy preferably selected from a therapy or treatment with
- bronchodilators, such as short and long-acting b2-agonists, anticholinergic agents,
- inhaled corticosteroids (ICS), or
- inhaled mucolytics, such as DNAse, hypertonic saline.

Transgenic Animals and Methods for Identifying miR-148 Modulators

As described above, the present invention provides transgenic, non-human mammals.

The transgenic animals of the invention are preferably miR-148 knock out or miR-148 induced knock out mammals, more preferably miR-148b knock out or miR-148b induced knock out mammals.

In one embodiment, the cells of a non-human mammal of the invention fail to express a functional micro RNA of the miR-148 family, said micro RNA of the miR-148 family being selected from miR-148a, miR-148b and miR-152.

In one embodiment, the cells of a non-human mammal of the invention comprise a coding region of a micro RNA of the miR-148 family, said micro RNA of the miR-148 family being selected from miR-148a, miR-148b and miR-152, under the control of a heterologous promoter active in the cells of said non-human mammal.

Preferably, the micro RNA is miR-148b.

Preferably, the transgenic mammal is a mouse.

As described above, the present invention provides methods for identifying modulator(s) of a micro RNA of the miR-148 family, said micro RNA of the miR-148 family being selected from miR-148a, miR-148b and miR-152, preferably modulator(s) of miR-148b.

Said method comprises:
(a) contacting a cell with a candidate compound;
(b) assessing miR-148 activity or expression; and
(c) comparing the activity or expression in step (b) with the activity or expression in the absence of the candidate compound, wherein a difference between the measured activities or expression indicates that the candidate compound is a modulator of a micro RNA of the miR-148 family selected from miR-148a, miR-148b and miR-152.

Preferably, the miR-148 micro RNA is miR-148b.

In one embodiment, the method comprises the use of the transgenic mammal of the invention.

Diagnostic and Prognostic Methods

As described above, the present invention provides methods for the diagnosis and/or prognosis of a chronic pulmonary disease.

Said method comprises determining expression levels of micro RNA of the miR-148 family selected from miR-148a, miR-148b and miR-152 in patient specimen, preferably of miR-148b.

The chronic pulmonary disease is preferably selected from chronic obstructive pulmonary disease (COPD), chronic bronchitis (CB), emphysema, cystic fibrosis (CF) lung disease, chronic lung disease (CLD) associated with premature birth, and other acquired and genetically determined forms of chronic lung diseases.

The patient specimen preferably comprises sputum, bronchoalveolar lavage fluid, blood, urine and lung tissue.

An upregulation of miR-148 expression or an increased miR-148 expression (preferably upregulation of miR-148b expression or an increased miR-148b expression) compared to a normal or control sample is indicative of a chronic pulmonary disease.

In one embodiment, miR-148 expression levels of the patient sample or specimens are determined at different time points, such as at the time of diagnosing a chronic pulmonary disease or at the time of beginning a therapy or during therapy. A change in the miR-148 expression levels at these different time points, when compared to the miR-148 expression levels of the first measured time point, can be an indication of the progression or advance of the chronic pulmonary disease in the patient or can be an indication whether the therapy is effective or not.

In one embodiment, miR-148 expression levels of the patient sample or specimens are determined for (early) diagnosing a chronic pulmonary disease, preferably for confirming such a diagnosis which was performed using other means or before such diagnosis using other means is established, performed or possible.

Preferably, miR-148 expression levels of the patient sample or specimens are determined when a chronic pulmonary disease is suspected on the basis of non-specific clinical symptoms, such as cough, or diagnostic findings comprising impaired lung function or morphological changes in chest X-ray, CT or MRI scans.

Diagnosis of COPD is performed on basis of clinical symptoms (cough), impaired lung function and morphological changes, i.e. bronchitis, mucus plugging, bronchiectasis, emphysema as determined from chest X-ray, chest CT scan or chest MRI scan. In CF as genetically determined form of COPD, diagnosis is confirmed by genetic testing, i.e. identification of mutations in the CFTR gene. However, cough is relatively non-specific symptom, so diagnosis at early stage remains difficult and that is where a new and specific diagnostic marker is of help.

The βENaC-transgenic (βENaC-Tg) mouse is an established model of chronic obstructive lung disease in humans (Mall et al., 2004, Mall et al., 2008). Specifically, βENaC-Tg mice develop a spontaneous lung disease that shares key features with CF, CLD, and COPD including airway mucus obstruction, reduced mucociliary clearance, chronic airway inflammation and emphysema. This established model was used here to identify miR-148b as a potential diagnostic and prognostic marker and test its role as therapeutic target of chronic obstructive lung disease in vivo as follows:

Using βENaC-Tg mice the inventors have shown:
Differentially expressed miRNAs in lungs from βENaC-Tg mice were identified (using microarray (miChip) profiling).
In particular, the expression of microRNA-148b is upregulated in βENaC-Tg mice.
Expression and localization of miR-148b in lungs of βENaC-Tg mice was shown.
In situ localization of miR-148b suggests its expression predominantly in airway epithelium and alveolar type II cells.
A miR-148b target gene was validated
Mig-6 is a direct target of miR-148b.
Functional significance of miR-148b in mouse lung was demonstrated.
An efficient knockdown of miR-148b by antagomir was shown.
Antagomir mediated knockdown of miR-148b prevents emphysema formation in βENaC-Tg mice.
Antagomir mediated knockdown of miR-148b reduces neutrophilic inflammation in βENaC-Tg mice.
Antagomir mediated knockdown of miR-148b reduces mucus in βENaC-Tg mice.
The knock-down studies of miR-148b by antagomir suggest functional role of miR-148b in COPD-like lung disease in βENaC-Tg mice.
Evaluation of therapeutic effects of miR-148b antagomir on pulmonary function of βENaC-Tg mice
Lung function testing in mice using pressure-volume curves shows that miR-148b antagomir treatment results in a significant reduction of increased lung compliance in βENaC-Tg mice indicative of reduced emphysema with improved respiratory mechanics of lung.
Measurements of total lung capacity (TLC) show that miR-148b antagomir treatment results in a significant reduction in elevated TLC in βENaC-Tg mice indicative of decreased alveolar destruction and reduced emphysema.
In humans, the inventors have shown:
Upregulation of miR-148b in airway cells from bronchial brushing from patients with Cystic Fibrosis (CF) and lung tissues from patients with COPD compared to disease-free tissues from human control subjects by qRT-PCR analysis.
Localization of miR-148b to airway and alveolar epithelial cells in human lungs tissue by in situ hybridization.

The following examples and drawings illustrate the present invention without, however, limiting the same thereto.

BRIEF DESCRIPTION OF THE DRAWINGS

The file of this patent/application contains at least one drawing executed in color. Copies of the patent with color drawings(s) will be provided by the Patent and Trademark Office upon request and payment of the necessary fee.

(A) Median intensity analysis of microRNAs differentially up- or downregulated in the lungs of mice with COPD-like lung disease (βENaC-Tg) relative to wild-type (WT) littermates at 3 days, 2 weeks and 6 weeks of age, as determined from microarray profiling (1.5 fold cut off, p<0.05, n=3-4 mice per group). (B) Validation of miRNA microarray results by quantitative real-time PCR (qRT-PCR) confirms upregulation of miR-148b in lungs from 6-week-old mice with COPD-like lung disease (βENaC-Tg) compared to wild-type (WT) controls. U6 small nuclear RNA was used as control for normalization.

Figure 1:
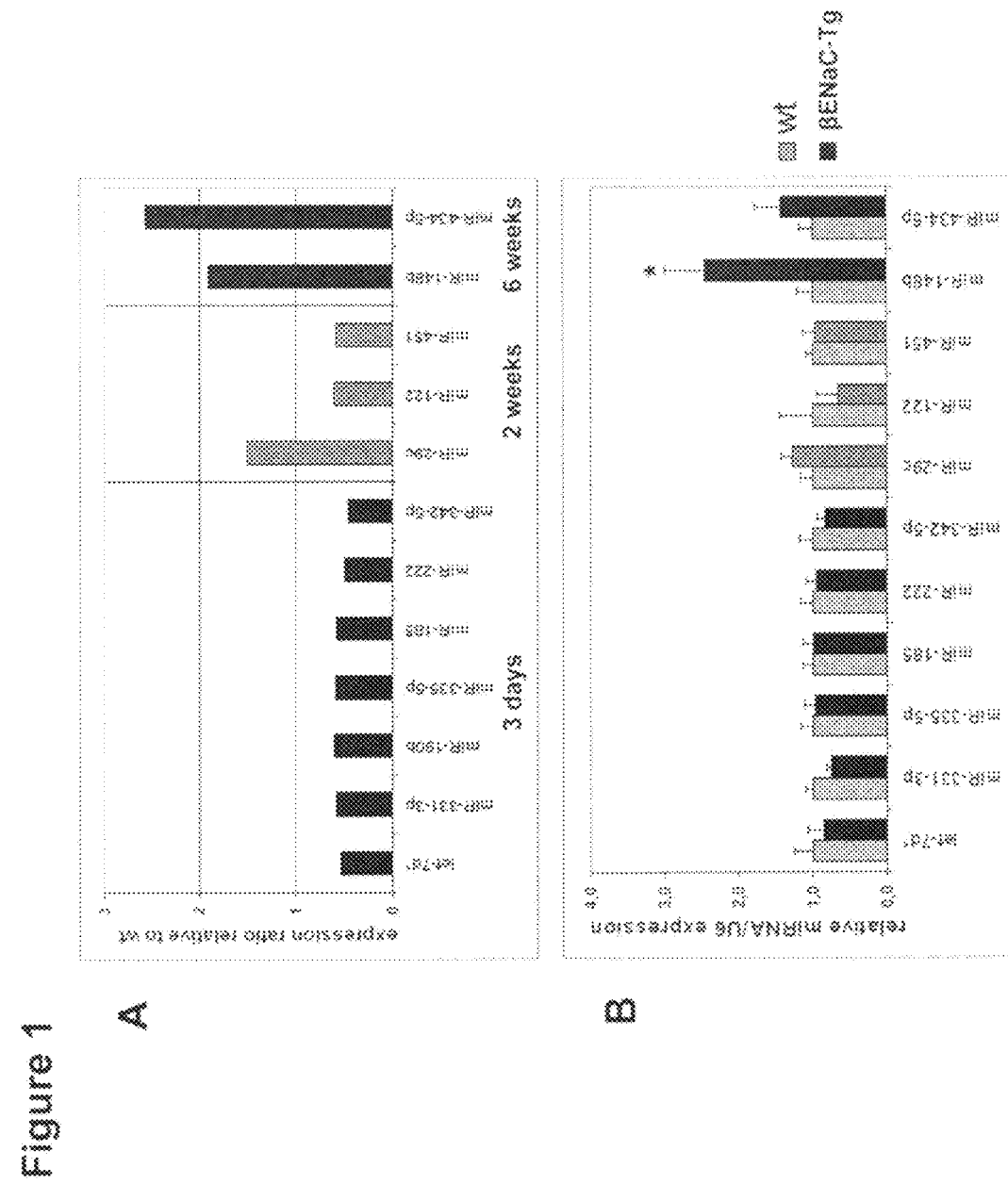
FIG. 1: Identification of differentially expressed miRNAs in lungs from mice with COPD-like lung disease.
Figure 2A:
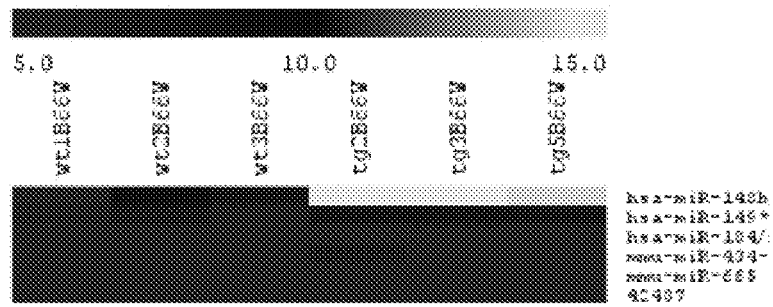
Figure 2B:
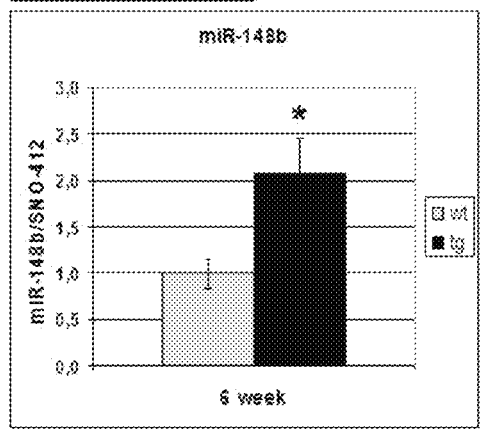
Figure 2C:
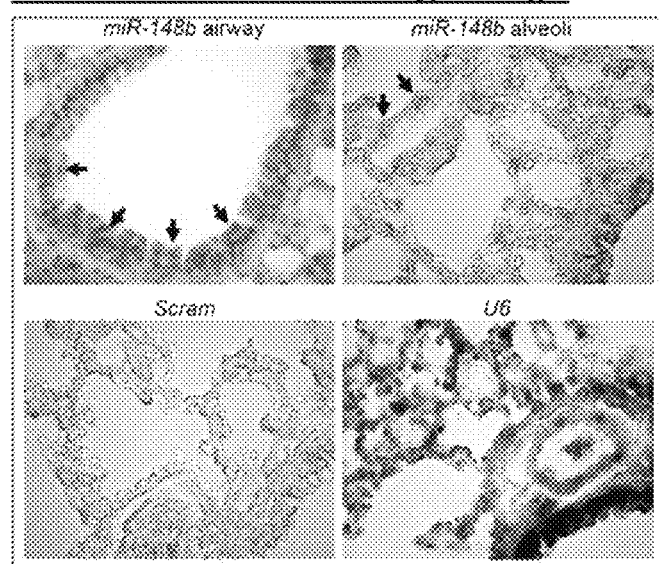

FIG. 2: Expression and localization of miR-148b in lungs of mice with COPD-like lung disease.

(A) Analysis of miRNA microarray results from 6-week-old mice with COPD-like lung disease (βENaC-Tg) and wild-type (WT) controls using Bioconductor R and Multiple Experiment Viewer software showing upregulation of miR-148b expression in βENaC-Tg mice. (B) Validation of miR-148b expression by quantitative real-time PCR (qRT-PCR) using SNO-412 small nucleolar RNA as control for normalization. Data represent mean±SEM, n=5 mice per group, P<0.05. (C) In situ hybridization localizes expression of miR-148b to airway and alveolar epithelial cells in lungs from wild-type mice as indicated by arrows (C) and βENaC-Tg mice (not shown). Representative of 3 mice per group. A probe with scrambled sequence (scram) unrelated to known miRNAs was used as a negative control and a probe for U6 was used as a positive control. Positive signals were visualized as dark blue/purple colour.

Figure 3C:
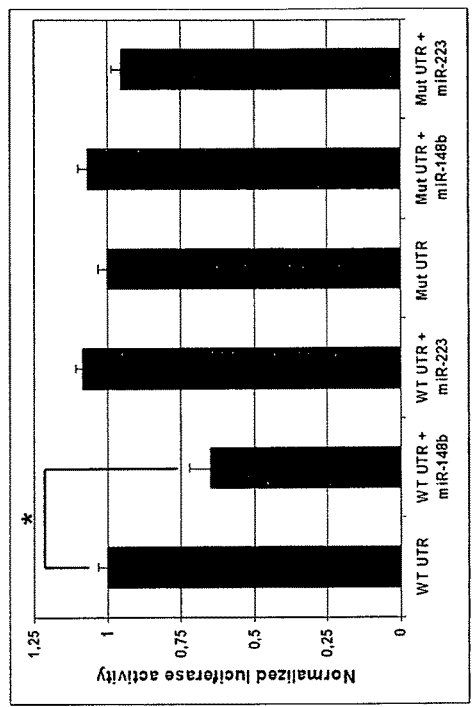

FIG. 3: In silico prediction and in vitro validation of Mig-6 as target of miR-148b.

(A) In silico analyses identified Pten, Slpr1, Errfi1 (Mig-6), Fbn1, Meox2, Can d1 as putative target genes of miR-148b with potential implications in lung phenotypes. (B) Luciferase reporter assay of Hela cells transfected with pmir-GLO-containing 3'UTR of putative target genes (Mig-6, S1PR1, Fibrillin) and Cand1) in the absence or presence of pCS2-pri-miR-148b showing repression of luciferase activity with Mig-6 3'UTR. (C) Luciferase reporter assay in Hela cells transfected with pmir-GLO-Mig-6-3'UTR (WT UTR) or pmir-GLO-Mig-6-3'UTR (Mut UTR) containing mutations in the "seed region" of potential miR-148 binding site, in the absence or presence of pCS2-pri-miR-148b or pCS2-pri-miR-223 vector showing specificity of the miR-148 binding site in the Mig-6 3'UTR. Firefly luciferase values were normalized to Renilla luciferase. Data represent mean±SEM, n=4 independent experiments, P<0.01.

Figure 4:
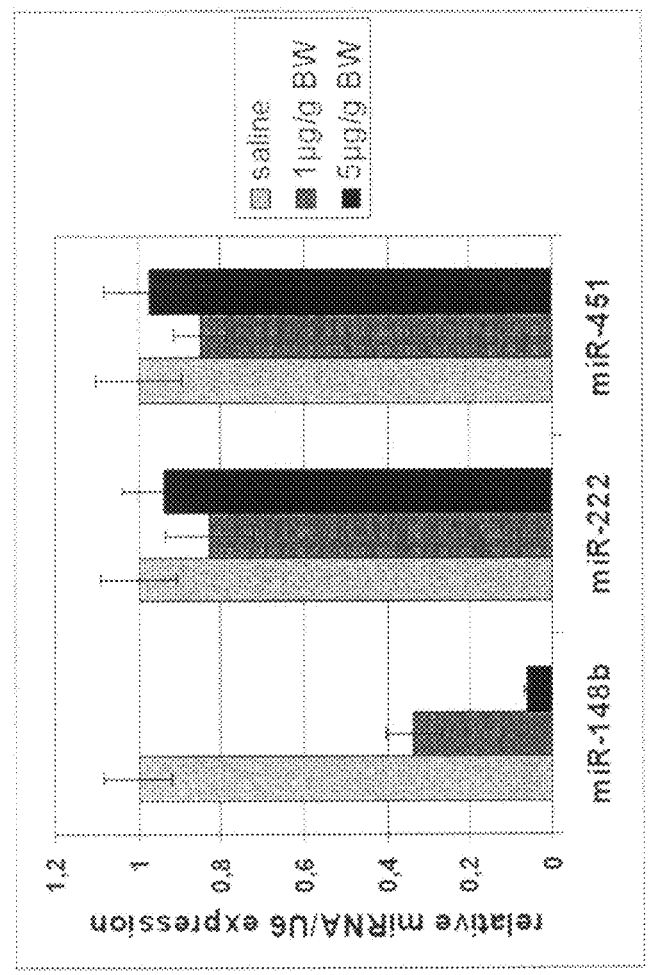

FIG. 4: Efficacy of in vivo knockdown of miR-148b expression in the lung by antagomir in mice.

Expression levels of miR-148b in lungs of wild-type mice after antagomir treatment by intranasal instillation (1 μg/g or 5 μg/g body weight (BW)) from the first day of life for 2 weeks (total of 9 instillations). Expression of miR-148b was largely abolished in mice treated with 5 μg/g body weight antagomir, whereas expression of miR-222 and miR-451 remained unchanged. Data represent mean±SEM, n=6-10 mice per group.

Figure 5A:
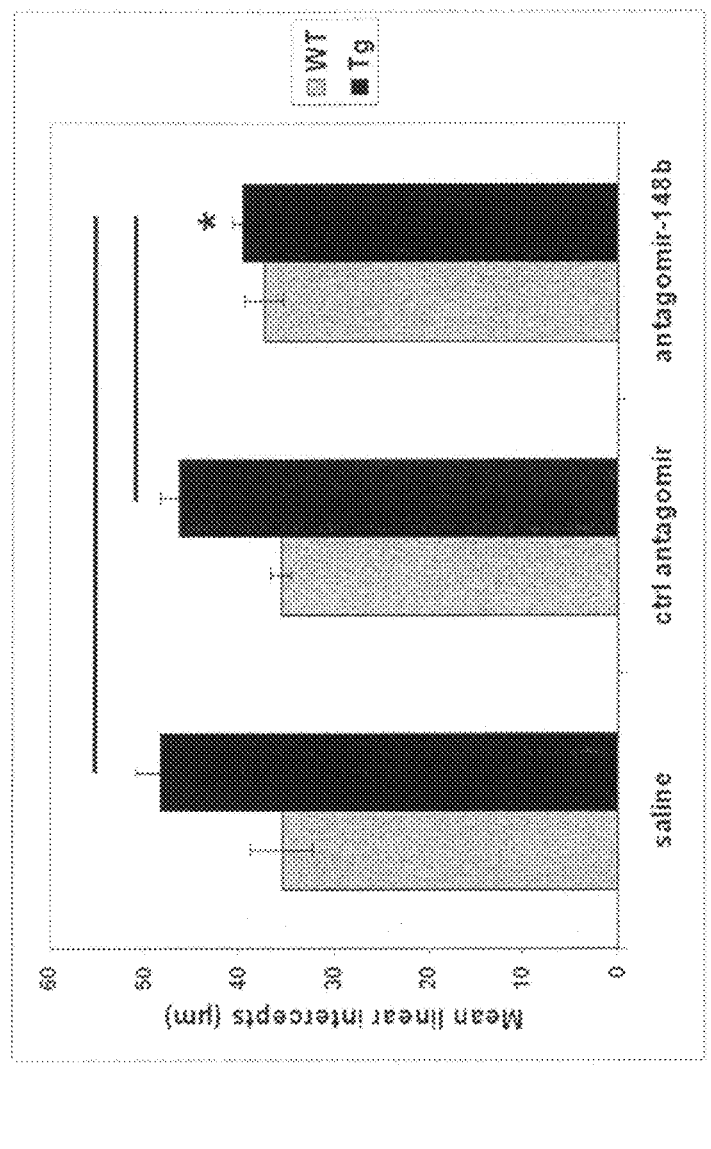
Figure 5B:
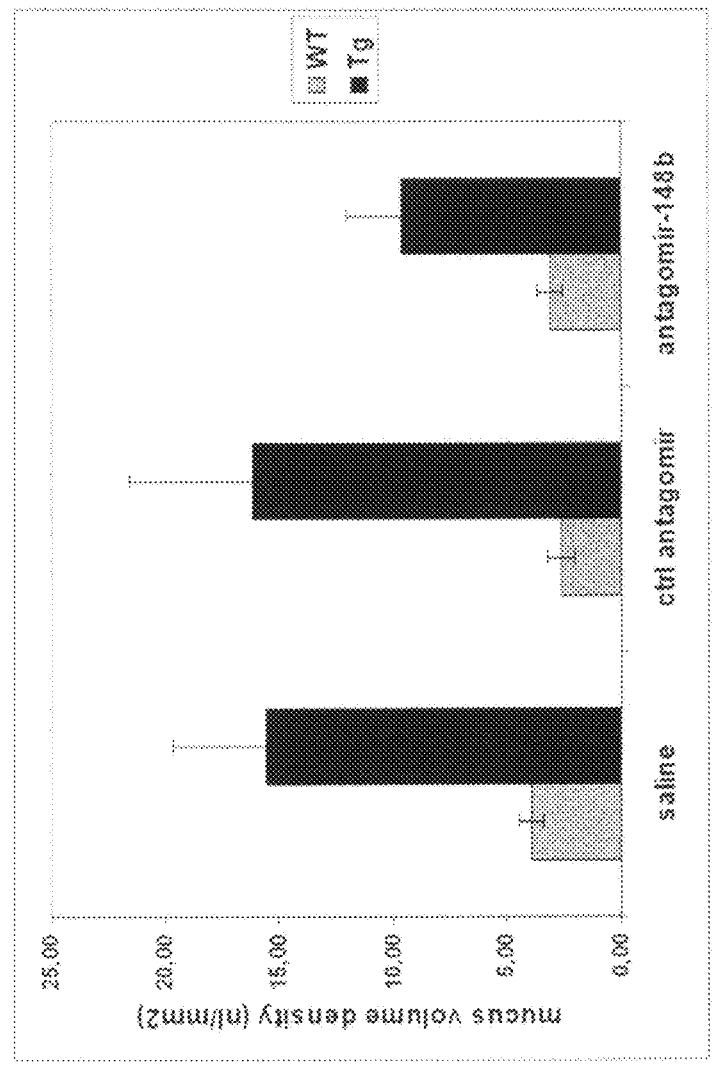
Figure 5C:
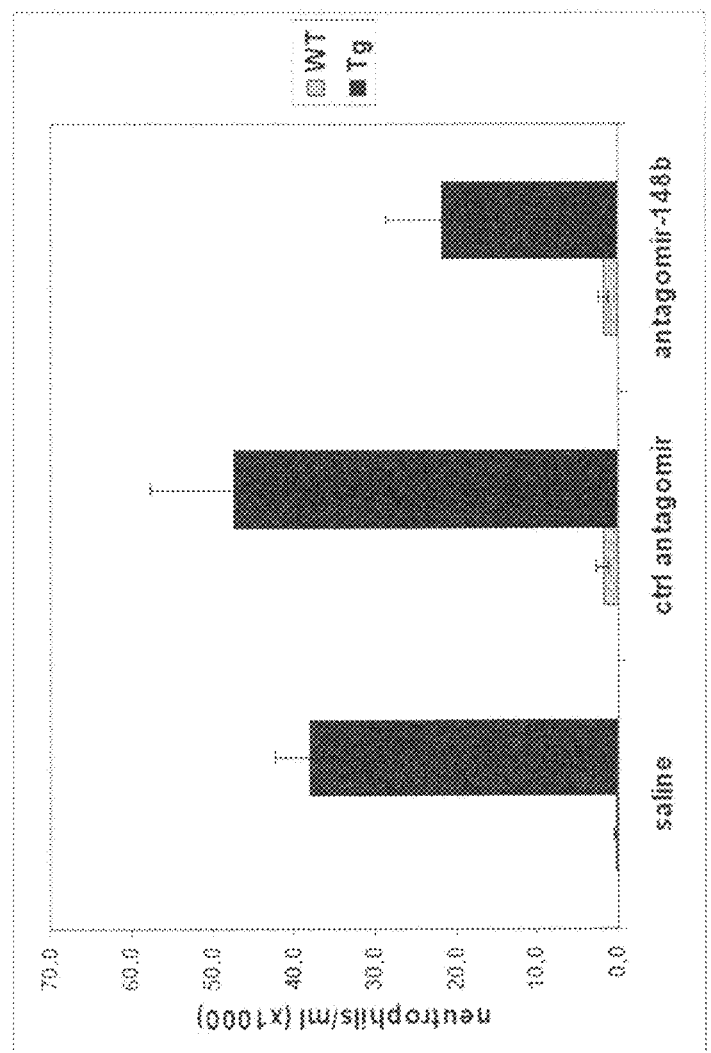

FIG. 5: Preclinical evaluation of therapeutic effects of miR-148b antagomir in COPD-like lung disease in mice.

(A-C) Mice with COPD-like lung disease (βENaC-Tg) and wild-type (WT) littermates were treated with miR-148b antagomir, control (mismatch) antagomir or vehicle alone. (A) Development of emphysema in βENaC-Tg mice, as determined from mean linear intercepts, was inhibited by preventive treatment with miR-148b antagomir. (B,C) Treatment with miR-148b antagomir reduced airway mucus obstruction (B) and neutrophilic airway inflammation, as determined from bronchoalveolar lavage (C) in βENaC-Tg mice. Data represent mean±SEM, n=7-8 mice per group, P<0.05.

Figure 6:
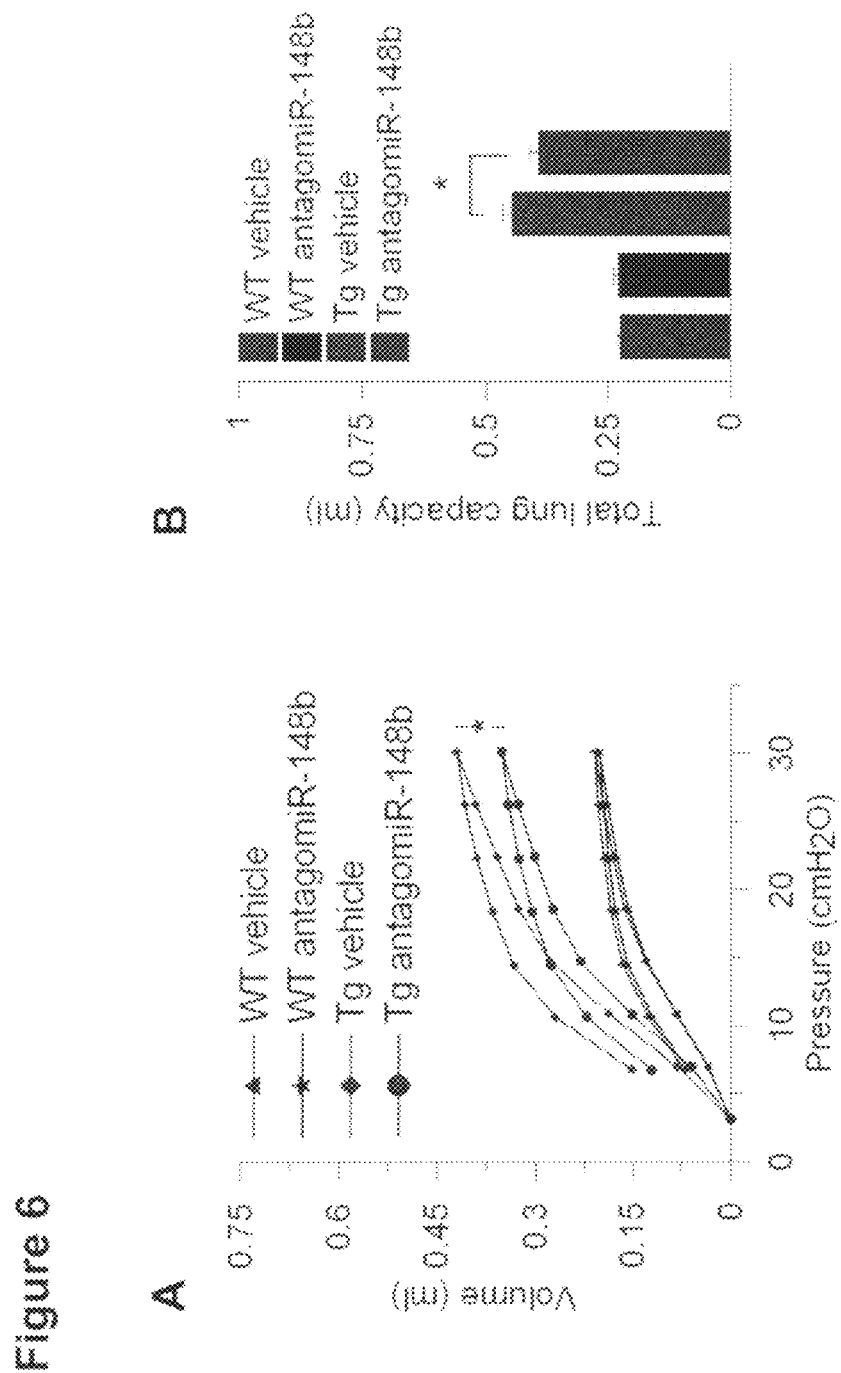

FIG. 6: Evaluation of therapeutic effects of miR-148b antagomir on pulmonary functions of βENaC-Tg mice.

(A) Pressure-volume curve. (B) Total lung capacity. Mice were treated with miR-148b antagomir or vehicle alone from day one of life until 3 weeks of age (total of 14 intranasal instillations, 5 µg/g body weight) and pulmonary function test was performed on day 23. Data represent mean±SEM, n=15-30 mice per group, P<0.05.

Figure 7:
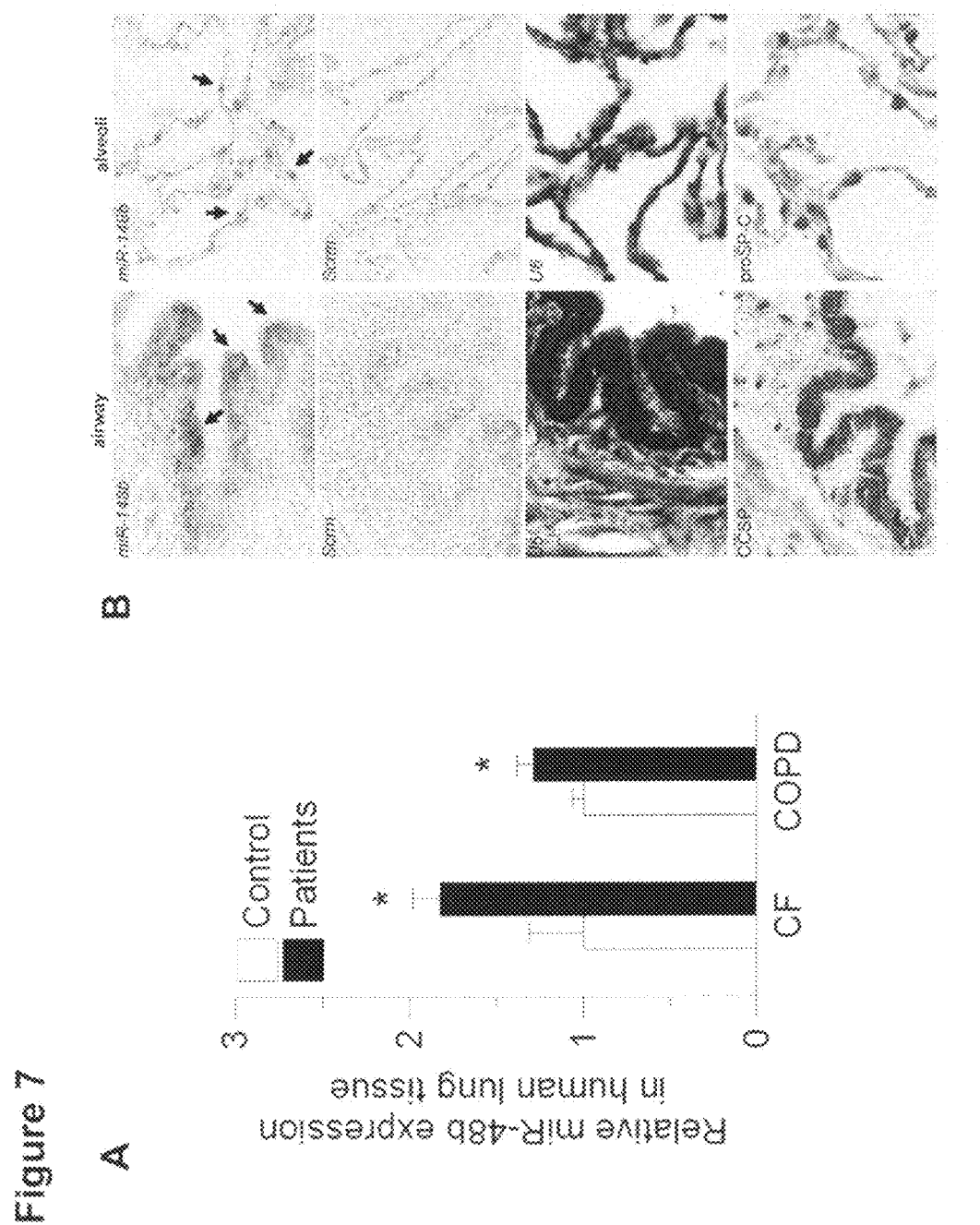

FIG. 7: Expression analysis of miR-148b in human lungs.

(A) Relative Q-PCR expression of miR-148b in bronchial brushing of Cystic Fibrosis (CF) and lung tissue of COPD I & II human subjects. Data represent mean±SEM, n=7 for CF group and 20-35 for COPD, P<0.05. (B) In situ hybridization shows expression of miR-148b to airway and alveolar epithelial cells in human lungs tissue. A scrambled sequence probe and U6 serve as a negative and positive control respectively. Immunostaining of CCSP (Clara Cell Secretory Protein) and proSP-C (pro surfactant protein C) serve as marker for non-cilliated epithelial cells in airway and alveolar type II cells in alveoli respectively.

EXAMPLES

1. Materials and Methods 1.1 Experimental Animals

All animal procedures in this study followed the protocols approved by Heidelberg University Animal Care and Use committee. The generation of βENaC-overexpressing (βENaC-Tg) mice has been previously described (Mall et al. Nat Med). The colony was maintained on a C57BL/6 background. βENaC-overexpressing mice were identified by PCR as described (Mall et al., 2004, Mall et al., 2008). Wild-type littermates served as controls in all experiments. Mice were housed in a specific pathogen-free animal facility and had free access to chow and water.

1.2 RNA Isolation, miRNA Microarray Profiling, and Quantitative Real-Time PCR Validation of miRNA Whole lungs were isolated on postnatal (P) day P3, P14 and 6 weeks from wild type and βENaC-Tg Mice. For each time point, there were at least three independent biological replicates. Total RNA from the lungs was isolated with the TRIzol reagent (Invitrogen) according to the manufacturer's instructions.

The miRNA microarrays were performed on genome-wide miRNA expression arrays platform (miChip) as previously described by Castoldi et al., 2008). The signal from each spot (miRNA) was analysed to the average median intensity from three biological replicates and by using Bioconductor R package (www.bioconductor.org) and MultiExperiment Viewer from TM4 Microarray Software Suite. Quantitative real-time PCR for miRNAs were performed with TaqMan Assays (Applied Biosystems) as per the company's protocols.

1.3 In Situ Hybridization

In situ hybridization for miRNAs was done with 5' DIG-labeled LNA probes (Exiqon) using non-radioactive method on paraffin section. Briefly, the slides containing sections of lung tissue were treated in proteinase K (Ambion) for 10 min at 37° C., fixed in 4% paraformaldehyde, and prehybridized in hybridization buffer (50% formamide, 5×SSC, 0.1% Tween 20, 9.2 mM citric acid, 50 µg/ml heparin, and 500 µg/ml yeast RNA, pH 6) in a humidified chamber. The 5' DIG-labeled LNA probes were then added to the sections at a 20 nM concentration and incubated overnight at the hybridization temperature [21° C. lower than the melting temperature (Tm) values of the specific probes]. The slides were rinsed in 2×SSC and washed three times for 30 min in 50% formamide, 2×SSC solution at the same hybridization temperature. This was followed by blocking with 2% sheep serum, 2 mg/ml BSA in PBS+0.1% Tween 20 (PBST) and incubation with anti-DIG-AP Fab fragments antibody (1:1,000) (Roche Applied Sciences) overnight at 4° C. in a humidified chamber. After washing in PBST and AP buffer (in mM: 100 Tris.HCl, pH 9.5, 50 $MgCl_2$, and 100 NaCl, with 0.1% Tween 20), the color reaction was carried out by incubation in BM Purple AP Substrate (Roche). The color reaction was stopped after observation of sufficient development of blue precipitate by washing with PBST. The slides were then mounted, coverslipped, and observed under Olympus IX-71 inverted microscope.

1.4 Luciferase Reporter Assay

3'UTRs of putative miR-148b target genes were PCR-amplified and cloned in pmir-GLO vector (Promega). The mutations in the seed region of miR-148b in Mig-6 3'UTRs were generated using the QuikChange Site-Directed Mutagenesis Kit (Stratagene). For the miRNA expression constructs, pri-miRNA precursors including ~200 bp flanking sequences were cloned into pCS2. Hela cells were transfected using TransIT-LTI Reagent (Mirus) with 50 ng of the pmir-GLO constructs and 500 ng of the miRNA vectors and processed using the Dual-Luciferase Reporter Assay (Promega) after 24 hours.

1.5 Synthesis of the miR-148b Antagomir

The single-stranded RNA 5'-acaaaguucugugaugcacuga-3' [SEQ ID NO. 16] was designed and then custom synthesized by Thermo Scientific Dharmacon. The sequence of the oligonucleotide was complementary to that of mmu-miR-148b.

Modifications:
all bases have 2'-O-methyl modifications,
the first two bases and the last four bases have phosphorothioate linkages, and
a cholesterol molecule was conjugated at the 3' end.

The mismatch control had the sequence

[SEQ ID NO. 17]
5'-acacacugcugcgacguaauga-3' and had the same modifications as the antagomir.

1.6 Antagomir Treatment Studies

The miR-148b antagomir and mismatch control antagomir were dissolved in normal saline (0.9% NaCl). βENaC-overexpressing (βENaC-Tg) mice and wild-type littermate controls were anesthetized with isoflurane 3% in oxygen and treated by intranasal instillation of miR-148b antagomir (5 µg/g body weight), mismatch control antagomir or vehicle alone on postnatal days 1, 2, 3, 6, 7, 8, 11, 12, and 13 and bronchoalveolar lavage (BAL) was performed and lungs were removed for histology and morphometry on day 14.

1.7 Bronchoalveolar Lavage Cell Counts (Neutrophils)

BAL of the right lobe was performed and cell counts were determined on cytospin preparations as previously described (Mall et al, 2008).

1.8 Mean Linear Intercepts

Right lung lobes were inflated at a constant pressure of 25 cm with 4% formalin, and processed for histology, sectioned at 5 µm, and stained with H&E. Mean linear intercepts were determined as previously described (Mall et al, 2008).

1.9 Mucus Density

The left lobe of lung was immersion fixed with 4% formalin, paraffin embedded, sectioned at two different levels and stained with alcian blue periodic acid-Schiff (AB-PAS). Airway mucus volume was obtained by measuring mucus volume density as previously described (Mall et al., 2008).

1.10 Pulmonary Function Testing

Mice were anesthetized with sodium pentobarbital (80 mg/kg), tracheostomized, and placed on the FlexiVent system (SCIREQ, Montreal, QC, Canada) for forced oscillatory measurements. Mice were then paralyzed with pancuronium bromide (0.5 mg/kg) to prevent spontaneous breathing. Mice were ventilated with a tidal volume of 11 mL/kg at a frequency of 150 breaths/min and a positive end expiratory pressure of 3 cm $H_2O$ to prevent alveolar collapse. Total lung capacity (TLC), and pressure-volume curves with stepwise increasing pressure (PVs-P) were consecutively measured as describe previously (Vanoirbeek et al, 2009). All perturbations were performed until three acceptable measurements.

1.11 Expression Analysis of miR-148b in Human Lungs.

Quantitative real-time PCR and in situ hybridization on human samples were performed using the methods described in paragraphs 1.2 and 1.3 of materials and methods section. Immunohistochemistry of paraffin embedded lung sections from human was performed using the methods as described previously (Duerr et al, 2011)

The features disclosed in the foregoing description, in the claims and/or in the accompanying drawings may, both separately and in any combination thereof, be material for realizing the invention in diverse forms thereof.

REFERENCES

Castoldi M, Schmidt S, Benes V, Hentze M W, Muckenthaler M U. miChip: an array-based method for microRNA expression profiling using locked nucleic acid capture probes. *Nat Protoc* 2008; 3:321-329.

Duerr J, Gruner M, Schubert S C, Haberkorn U, Bujard H, Mall M A. Use of a new-generation reverse tetracycline transactivator system for quantitative control of conditional gene expression in the murine lung. *Am J Respir Cell Mol Biol* 2011; 44(2):244-54. Grimson A, Farh K K, Johnston W K, Garrett-Engele P, Lim L P, Bartel D P. MicroRNA targeting specificity in mammals: determinants beyond seed pairing. Molecular Cell 2007, 27(1): 91-105.

Harkema J R, Plopper C G, Hyde D M, St George J A. Regional differences in quantities of histochemically detectable mucosubstances in nasal, paranasal, and nasopharyngeal epithelium of the bonnet monkey. *J Histochem Cytochem* 1987; 35:279-286.

Ji X, Takahashi R, Hiura Y, Hirokawa G, Fukushima Y, Iwai N. Plasma miR-208 as a biomarker of myocardial injury. *Clin Chem.* 2009 November; 55(11):1944-9.

Krek A, Grün D, Poy M N, Wolf R, Rosenberg L, Epstein E J, MacMenamin P, da Piedade I, Gunsalus K C, Stoffel M, Rajewsky N. Combinatorial microRNA target predictions. *Nat Genet.* 2005 May; 37(5):495-500.

Krützfeldt J, Rajewsky N, Braich R, Rajeev K G, Tuschl T, Manoharan M, Stoffel M. Silencing of microRNAs in vivo with 'antagomirs'. *Nature.* 2005 Dec. 1; 438(7068): 685-9.

Mall M, Grubb B R, Harkema J R, O'Neal W K, Boucher R C. Increased airway epithelial $Na^+$ absorption produces cystic fibrosis-like lung disease in mice. *Nat Med* 2004; 10:487-493.

Mall M A, Harkema J R, Trojanek J B, Treis D, Livraghi A, Schubert S, Zhou Z, Kreda S M, Tilley S L, Hudson E J, O'Neal W K, Boucher RC. Development of chronic bronchitis and emphysema in beta-epithelial Na+ channel-overexpressing mice. *Am J Respir Crit Care Med* 2008; 177:730-742.

Maragkakis M, Reczko M, Simossis V A, Alexiou P, Papadopoulos G L, Dalamagas T, Giannopoulos G, Goumas G, Koukis E, Kourtis K, Vergoulis T, Koziris N, Sellis T, Tsanakas P, Hatzigeorgiou AG. DIANA-microT web server: elucidating microRNA functions through target prediction. Nucleic Acids Res 2009, 37(Web Server issue):W273-276.

Vanoirbeek J A et al, *Am J Respir Cell Mol Biol* 2009; 42:96-104.

Weibel E R. Morphometry of the human lung. Berlin: Springer Verlag, 1963.

Weibel E R, Hsia C C, Ochs M. How much is there really? Why stereology is essential in lung morphometry. *J Appl Physiol* 2007; 102:459-467.

---

The invention claimed is:

1. A method of treating a chronic pulmonary disease selected from chronic obstructive pulmonary disease (COPD) and cystic fibrosis (CF) lung disease, in a subject in need thereof, the method comprising:
inhibiting a micro RNA 148b (miR-148b) expression and/or activity by administering to the subject an effective amount of at least one inhibitor of miR-148b, wherein the at least one inhibitor of miR-148b comprises a sequence complementary to at least 13 contiguous nucleotides of a nucleotide sequence of SEQ ID NO:1 or a sequence having at least 95% sequence identity to a nucleotide sequence of SEQ ID NO:1.

2. The method according to claim 1, wherein the at least one miR-148b inhibitor is 13 to 22 nucleotides in length; and wherein the at least one miR-148b inhibitor comprises at least one 2'-O-modified nucleotide.

3. The method according to claim 2, wherein the at least one miR-148b inhibitor comprises RNA, LNA, or combinations thereof.

4. The method according to claim 2, wherein the at least one miR-148b inhibitor sequence is 20 to 22 nucleotides in length.

5. The method according to claim 2, wherein the at least one miR-148b inhibitor comprises one or more phosphorothioate linkages.

6. The method according to claim 2, wherein the at least one miR-148b inhibitor is conjugated at an end.

7. The method according to claim 6, wherein the at least one miR-148b inhibitor is conjugated with a hydrophobic moiety.

8. The method according to claim 7, wherein the hydrophobic moiety is cholesterol.

9. The method according to claim 2, wherein the at least one miR-148b inhibitor comprises a cellular delivery construct or carrier for the oligonucleotide.

10. The method according to claim 9, wherein the at least one miR-148b inhibitor comprises an expression vector, a virus or parts thereof, or a liposome.

11. The method according to claim 2, wherein the at least one miR-148b inhibitor is an antagomir of miR-148b.

12. The method according to claim 2, wherein the at least one miR-148b inhibitor is administered to a subject in need thereof by inhalation, intravenous, oral, suppository, or sublingual administration.

13. The method according to claim 12, wherein inhalation administration is as aerosol, dry powder, solution, or sustained release aerosol, powder or solution.

14. The method according to claim 2, wherein the at least one miR-148b inhibitor is administered to a subject in need thereof in combination with a second pulmonary therapy.

15. The method according to claim 14, wherein said second therapy is selected from a therapy or treatment with bronchodilators, inhaled corticosteroids (ICS) or inhaled mucolytics.

* * * * *